United States Patent [19]

Cragoe, Jr. et al.

[11] 4,066,675

[45] Jan. 3, 1978

[54] 9-THIA- AND OXOTHIA- AND 9-DIOXOTHIA-11,12-SECO-PROSTAGLANDINS AND PROCESSES

[75] Inventors: Edward J. Cragoe, Jr.; John B. Bicking; Robert L. Smith, all of Lansdale, Pa.

[73] Assignee: Merck & Co., Inc., Rahway, N.J.

[21] Appl. No.: 743,821

[22] Filed: Nov. 22, 1976

Related U.S. Application Data

[60] Division of Ser. No. 669,006, March 22, 1976, Pat. No. 4,018,802, which is a continuation-in-part of Ser. No. 566,566, April 9, 1974, abandoned, which is a continuation-in-part of Ser. No. 483,178, June 25, 1974, abandoned.

[51] Int. Cl.$^2$ .......................................... C07C 143/90
[52] U.S. Cl. ................................... 260/400; 260/401; 260/402; 424/312; 424/314; 424/318; 424/320
[58] Field of Search ...................... 260/400, 401, 402; 424/312, 314, 318, 320

[56] References Cited

U.S. PATENT DOCUMENTS 3,975,427  8/1976  Untch .............................. 260/400 X

FOREIGN PATENT DOCUMENTS 806,639  4/1974  Belgium.

OTHER PUBLICATIONS

Chemical Abstracts, vol. 83, No. 7 : 58134b.

Primary Examiner—Winston A. Douglas
Assistant Examiner—John F. Niebling
Attorney, Agent, or Firm—Thomas E. Arther; Harry E. Westlake, Jr.; Rudolph J. Anderson, Jr.

[57] ABSTRACT

This invention relates to 9-thia-, 9-oxothia, and 9-dioxothia-11,12-seco-prostaglandins and processes for their manufacture. These compounds have prostaglandin-like biological activity and are particularly useful for the treatment of skin diseases such as psoriasis, for the prevention of thrombus formation, in stimulating the production of growth hormone in intact animals, and as regulators of the immune response.

11 Claims, No Drawings

1

9-THIA- AND OXOTHIA- AND 9-DIOXOTHIA-11,12-SECO-PROSTAGLANDINS AND PROCESSES

This is a division of application Ser. No. 669,006 filed Mar. 22, 1976, now U.S. Pat. No. 4,018,802 issued Apr. 19, 1977, which in turn is a continuation-in-part of U.S. Ser. No. 566,566 filed Apr. 9, 1974 and now abandoned; which in turn is a continuation-in-part of U.S. Ser. No. 483,178 filed June 25, 1974 and now abandoned.

SUMMARY OF THE INVENTION

This invention relates to novel 9-thia-(including 9-oxothia- and 9-dioxothia-)11,12-seco-prostaglandins. These compounds can be represented by the following structural formula:

$$R^1-S(O)_n-\overset{*}{C}H-CH_2-Y-CH_2-A-CH_2-R \quad (I)$$
$$\underset{R^2\quad OR^3}{CH_2-Z-\overset{\psi}{C}-\overset{\psi}{C}(R^4)_2-R^5}$$

wherein R is selected from the group consisting of carboxy and a carboxy salt, said salt being formed from a pharmaceutically acceptable cation, such as metal cations derived from alkali metals, alkaline earth metals, and amines such as ammonia, primary and secondary amines, and quaternary ammonium hydroxides. Especially-preferred metal cations are those derived from alkali metals, e.g., sodium, potassium, lithium, and the like and alkaline earth metals, e.g., calcium, magnesium, and the like and other metals, e.g., aluminum, iron and zinc.

Pharmaceutically acceptable cations derived from primary, secondary, or tertiary amines, or quaternary ammonium hydroxides are methylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethyl ammonium hydroxide, tetraethylammonium hydroxide, benzyltrimethylammonium and the like.

R is also selected from alkoxycarbonyl (—COOR$^6$) wherein R$^6$ is alkyl having 1-10 carbon atoms, carbamoyl (—CONH$_2$); substituted carbamoyl (—CONR$^7$R$^8$) wherein R$^7$ and R$^8$ are selected from the group consisting of hydrogen, lower alkyl having 1-4 carbon atoms and diloweralkylaminoalkyl having 4-7 carbon atoms; and carbazoyl (—CONHNH$_2$).

A is selected from the group consisting of methylene (—CH$_2$—) and oxygen (—O—).

Y is selected from the group consisting of ethylene (—CH$_2$—CH$_2$—), cis-(or z-)vinylene $$(-\overset{H}{\underset{}{C}}=\overset{H}{\underset{}{C}}-), \text{ trans-(or e-)vinylene } (-\overset{H}{\underset{}{C}}=\overset{}{\underset{H}{C}}-),$$

or ethynylene (—C≡C—).

n = 0, 1, or 2.

R$^1$ is selected from the group consisting of methyl, ethyl, 2-hydroxyethyl, 2-(loweralkyloxy)ethyl, and vinyl.

Z is selected from the group consisting of ethylene, vinylene or ethynylene.

R$^2$ is independently selected from the group consisting of hydrogen and methyl.

R$^3$ is selected from the group consisting of hydrogen, and lower alkanoyl of 1-5 carbon atoms, e.g., formyl, acetyl, propionyl, butyryl, isobutyryl, valeryl, pivaloyl and the like.

R$^4$ is independently selected from the group consisting of hydrogen and methyl.

R$^5$ is selected from the group consisting of alkyl or branched alkyl of 3-6 carbon atoms (e.g., propyl, butyl, hexyl, isoamyl, 3,3-dimethylbutyl), vinyl or 4,4,4-trifluorobutyl.

Further:

In addition, when R$^5$ is straight chain alkyl and R$^2$ is methyl, the terminal carbon atom of R$^5$ can be joined to R$^2$ (with abstraction of hydrogen) to form a carbocyclic ring of from 6-9 carbon atoms, or when R$^5$ is straight chain alkyl and R$^2$ is hydrogen, the terminal carbon atom of R$^5$ can be joined to the carbon bearing OR$^3$ to form a carbocyclic ring of from 5-8 carbon atoms.

Further, R$^5$ can be OR$^{5a}$ where R$^{5a}$ is alkyl, branched alkyl of from 2-5 carbon atoms, substituted alkyl including 3,3,3-trifluoropropyl, 5- or 6-membered heterocyclic ring containing nitrogen or oxygen including pyridyl, furyl or furfuryl, or phenyl in which the phenyl ring can be substituted with one or two substituents selected from the group consisting of halogen, methyl, methoxy, or trifluoromethyl.

It is to be recognized that the carbon atom marked by an asterisk (*) and, in some instances, the carbon atoms marked by a dagger ($\psi$) are chiral. In addition, certain carbon atoms included in R$^5$ are also chiral. The compounds of this invention are understood to include the individual stereoisomers and mixtures of stereoisomers, the biological activity of which will vary but which may readily be determined in the in vitro and in vivo assays described hereinbelow.

A preferred embodiment of this invention relates to the 11,12-secoprostaglandins having the general formula:

$$H_3C\diagdown^{SO_2}\diagdown_{CH}\diagdown^{CH_2}\diagdown_{Y-CH_2}\diagdown^{CH_2}\diagdown_{CH_2}\diagdown^{COOH}$$
$$\underset{R^2\quad OH}{CH_2-Z-C-C(R^4)_2-R^5}$$

wherein

Z is ethylene, vinylene, or ethynylene;

R$^2$ and R$^4$ are as defined above;

Y is selected from the group consisting of ethylene, cis-vinylene, or ethynylene; and R$^5$ is alkyl, branched chain alkyl of 3-6 carbon atoms, vinyl, 4,4,4-trifluorobutyl, or OR$^{5a}$ wherein R$^{5a}$ is as defined above.

It is to be noted that the carbon bearing R$^2$ and OR$^3$ is asymmetric. This invention includes stereo-isomers in which this asymmetric center is exclusively in either one or the other of the two possible configurations, R and S.

BACKGROUND OF THE INVENTION

The compounds of Formula I are described as 11,12-seco-prostaglandins because of their structural relationship to the naturally occurring prostaglandins.

The prostaglandins constitute a biologically prominent class of naturally occurring, highly functionalized $C_{20}$ fatty acids; namely, 8,11,14-eicosatrienoic acid, 5,8,11,14-eicosatetraenoic acid and 5,8,11,14,17-eicosapentaenoic acid. Each known prostaglandin is a formal derivative of the parent compound, termed 'prostanoic acid'; the latter is a $C_{20}$ fatty acid covalently bridged between carbons 8 and 12 such as to form a trans, vicinally-substituted cyclopentane in which the carboxy-bearing side chain is 'alpha' or below the plane of the ring and the other side chain is 'beta' or above the plane of the ring as depicted in Formula III:

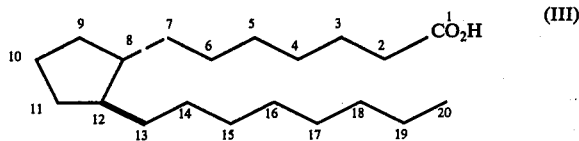

Within the last decade, prostaglandins have been shown to occur extensively in low concentrations in a myriad of mammalian tissues where they are both rapidly anabolized and catabolized and to exhibit a vast spectrum of pharmacological activities including prominent roles in (a) functional hyperemia, (b) the inflammatory response, (c) the central nervous system, (d) transport of water and electrolytes, and (e) regulation of cyclic AMP. Further details concerning the prostaglandins can be found in recent reviews of their chemistry [J. E. Pike, Fortschr. Chem. Org. Naturst., 28, 313 (1970)] and G. F. Bundy, A. Rep. in Med. Chem., 7, 157 (1972)], biochemistry [J. W. Hinman, A. Rev. Biochem., 41, 161 (1972)], pharmacology [J. R. Weeks, A. Rev. Pharm., 12, 317 (1972)], physiological significance [E. W. Horton, Physiol. Rev., 49, 122 (1969)] and general clinical application [J. W. Hinman, Postgrad. Med. J., 46, 562 (1970)].

The potential application of natural prostaglandins as medicinally useful therapeutic agents in various mammalian disease states is obvious but suffers from three formidable major disadvantages; namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug, and (c) although limited quantities of prostaglandins are presently produced by both chemical and biochemical processes, their production cost is extremely high; and, consequently, their availability is quite restricted.

Our interest has, therefore, been to synthesize novel compounds structurally related to the natural prostaglandins but with the following unique advantages: (a) simplicity of synthesis leading to low cost of production; (b) specificity of biological activity which may be either of a prostaglandin-mimicking or prostaglandin-antagonizing type; (c) enhanced metabolic stability. The combination of these advantages serves to provide effective, orally and parenterally active therapeutic agents for the treatment of certain human and animal diseases. Included are applications in the control of the immune response, blood clotting, and skin diseases such as psoriasis.

A number of publications describe the preparation of compounds said to be structurally related to prostaglandins. These publications include German Pat. No. 2,354,085 dated May 16, 1974 which describes certain substituted 11,12-secoprostaglandins which are said to have prostaglandin activity when orally administered. However, the present invention contemplates entirely different derivatives of 11,12-secoprostaglandins which have a different spectrum of biological activity as set forth hereinafter.

The compounds of the present invention are useful as pharmaceutically active compounds. Thus, these compounds are orally active in the treatment of conditions which are responsive to the actions of the natural prostaglandins. It is, of course, necessary to determine by routine laboratory testing which of the compounds of the present invention are most suitable for a specific end use. Some of the compounds of the invention have prostaglandin-like activity in that they mimic the effect of prostaglandin $E_1$ in stimulating the formation of cyclic AMP in the mouse ovary in vitro. Certain of the compounds of the present invention raise the cyclic AMP levels in normal human skin (obtained from mastectomy), psoriatic plaques, and "normal adjuvant" skin tissue, all in an in vitro assay. Examples of the compounds which are particularly effective in this noted in vitro assay are:

a. 8-methylsulfonyl-12-hydroxyheptadecanoic acid
b. 8-methylsulfinyl-12-hydroxyheptadecanoic acid
c. 8-(2-hydroxyethylsulfonyl)-12-hydroxyheptadecanoic acid
d. 8-methylsulfonyl-12-hydroxy-13-(4-fluorophenoxy)tridecanoic acid Because of the response in the above-noted in vitro assay, these compounds are indicated as useful in the treatment of a variety of skin diseases including psoriasis, atopic dermatitis, non-specific dermatitis, forms of dermatitis due to irritation, allergic extrinsic dermatitis, scaly skin-cell carcinoma, lamella, ichthyosis, epidermolytic hyperkeratosis, pre-malignant keratosis induced by sun, non-malignant keratosis, acne, and seborrheic dermatitis in humans, as well as atopic dermatitis and mange in domestic animals.

In addition, certain of the compounds of this invention are particularly effective in inhibiting the aggregation in platelets in blood stimulated with collagen to cause platelet aggregation; and thus, in inhibiting platelet aggregation, they are useful in preventing thrombus formation. Examples of these compounds are:

a. 8-methylsulfonyl-12-hydroxyheptadecanoic acid
b. 8-methylsulfinyl-12-hydroxyheptadecanoic acid
c. 9-(2-hydroxyethylsulfonyl)-12-hydroxyheptadecanoic acid
d. 8-methylsulfonyl-12-hydroxy-13-(4-fluorophenoxy)tridecanoic acid In addition, certain of the compounds of this invention are particularly effective in causing the release of growth hormone from pituitary glands in both in vivo and in vitro assays.

In a typical in vitro assay, rats are decapitated and the pituitary gland removed. The anterior pituitary gland is divided in two and one of the resulting hemipituitary sections is placed in a control bath of Kreb's Ringer bicarbonate buffer solution. The other hemipituitary gland section is placed in a similar buffer to which is added 2 ml. of the test solution of measured concentration of test compound. After a one-hour period, both the control bath and the test bath are analyzed for growth hormone production using a radioimmuno assay.

In an in vivo assay for measuring the stimulation of growth hormone production, male Holzmann rats are fasted overnight and anesthetized. Both the carotid artery and the jugular vein are canulated, thus providing access to the circulating blood entering and exiting the animal brain. A control blood sample is removed from the jugular vein prior to administration of the test compound. The test compound is then injected into the carotid artery and samples of the blood from the jugular vein taken at 10, 20, and 40 minutes following injection of the test compound. Both control samples and samples following administration of the test compound are analyzed for the presence of growth hormone by radioimmuno assay. Increase of growth hormone caused by the test compound is noted by reference to the amount of growth hormone in the control sample. Compounds found to be active in these tests are useful in stimulating growth hormone in poorly-functioning pituitary glands.

An example of a compound which is active in each of the in vitro and in vivo tests above is 8-methylsulfonyl-12-hydroxyheptadecanoic acid.

The compounds of this invention are also indicated to be useful in therapy as regulators of the immune response. The basis for their activity in this area is their ability to stimulate cyclic-AMP formation in cells. Agents, including the E prostaglandins, that increase cellular cyclic-AMP concentration, interfere with the cell-mediated immune response by inhibiting lymphocyte expression in response to antigen, by inhibiting release of pathological mediators from sensitized lymphocytes, and by inhibiting the killing of target cells by such lymphocytes. Various assays which depend upon the measurement of some function of the immunologically competent lymphocyte can be used to demonstrate that the prostaglandin analogs of this invention are similarly active. For example, the release of lymphokines (proteins that are agents of inflammation and tissue destruction) from sensitized lymphocytes in culture is strongly inhibited by these analogs in low concentrations. Thus, it is apparent that the compounds of this invention are applicable to the treatment of those autoimmune diseases in whose pathogenesis a cell-mediated immune reaction is involved. Such diseases range from contact dermatitis to such chronic destructive diseases as rheumatoid arthritis and possibly multiple sclerosis and systemic lupus erythematosus.

The present prostaglandin analogs are also effective in preventing the rejection of transplanted organs. The biochemical basis for this action is the same as outlined in the preceding paragraph, for the rejection of organ grafts is considered to be predominantly a cell-mediated immune phenomenon and the hallmark of organ rejection is the infiltration of cytotoxic lymphocytes into the graft. Direct evidence that the compounds of this invention can retard or prevent transplant rejection has been obtained in the rat renal allograft model; in this system, administration of the compounds of the present invention prevents the rejection of the transplanted kidney and the subsequent death of the host rat, which events invariably occur in the cases of untreated rats or those treated with the immunosuppressants.

An example of a compound which is an effective regulator of the immune responses of the types described above is 8-methylsulfonyl-12-hydroxyheptadecanoic acid.

Because of their biological activity and ready accessibility, the compounds of the invention are also useful in that they permit large scale animal testing useful and necessary to understanding of these various disease conditions such as dwarfism caused by poorly-functioning pituitary glands, stroke (thrombus formation), skin diseases such as psoriasis, and the like. It will be appreciated that not all of the compounds of this invention have these biological activities to the same degree but the choice of any particular ones for any given purpose will depend upon several factors including the disease state to be treated.

The compounds of this invention can be administered either topically or systemically (i.e., intravenously, subcutaneously, intramuscularly, orally, rectally, or by aerosolization in the form of sterile implants for long action).

The pharmaceutical compositions can be sterile injectable suspensions or solutions, or solid orally administrable pharmaceutically acceptable tablets or capsules; the compositions can also be intended for sublingual administration, or for suppository use. It is especially advantageous to formulate compositions in dosage unit forms for ease and economy of administration and uniformity of dosage. 'Dosage unit form' as a term used herein refers to physically discrete units suitable as unitary dosages for animal and human subjects, each unit containing a predetermined quantity of active material calculated to produce the desired biological effect in association with the required pharmaceutical means.

Illustratively, a sterile injectable composition can be in the form of aqueous or oleagenous suspensions or solutions.

The sterile injectable composition can be an aqueous or oleagenous suspension or solution. Suspensions can be formulated according to the known art using suitable dispersing and wetting agents and suspending agents. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative; for example, methylparaben, propylparaben, phenol, and chlorobutanol. The aqueous vehicle can also contain sodium chloride, preferably in an amount to be isotonic; as well as a suspending agent, for example, gum arabic, polyvinyl pyrrolidone, methyl cellulose, acetylated monoglyceride (available commercially as Myvacet from Distillation Products Industry, a division of Eastman Kodak Company), monomethyl glyceride, dimethyl glyceride or a moderately high molecular weight polysorbitan (commercially available under the tradenames Tween or Span from Atlas Powder Company, Wilmington, Delaware). Other materials employed in the preparation of chemotherapeutic compositions containing the compound may include glutathione, 1,2-propanediol, glycerol and glucose. Additionally, the pH of the composition is adjusted by use of an aqueous solution such as tris(hydroxymethyl)-aminomethane (tris buffer).

Oily pharmaceutical carriers can also be used, since they dissolve the compound and permit high doses. Many oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2–50 mg./ml. Lower concentrations require needless quantities of liquid. Higher concentrations than 50 mg./ml. are difficult to maintain and are preferably avoided.

Oral administration forms of the drug can also be prepared for laboratory animals or human patients provided that they are encapsulated for delivery in the gut. The drug is subject to enzymatic breakdown in the acid environment of the stomach. The same dosage levels can be used as for injectable forms; however, even higher levels can be used to compensate for biodegradation in the transport. Generally, a solid unit dosage form can be prepared containing from 0.5 mg. to 25 mg. active ingredient.

Whatever the mode of administration, doses in the range of about 0.10 to 20 milligrams per kilogram of body weight administered one to four times per day are used, the exact dose depending on the age, weight, and condition of the patient, and the frequency and route of administration.

The low cost and ready accessibility of the compounds of this invention make them particularly promising for applications in veterinary medicine in which field their utilities are comparable to those in human medicine.

PROCESSES FOR THE SYNTHESIS OF COMPOUNDS OF THIS INVENTION

One of the preferred groups of compounds of the present invention is represented by the formula

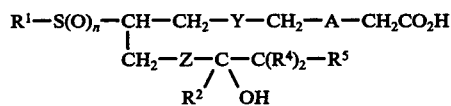

wherein $R^1$, $n$, Y, A, Z, $R^2$, $R^4$ and $R^5$ are as previously defined. Three principal methods are employed in the synthesis of compounds of this general type.

The first method of synthesis is useful in the preparation of a preferred sub-group of compounds of the formula

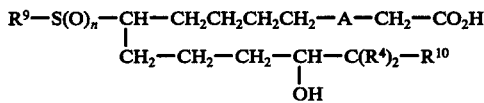 (II)

wherein A, $R^4$ and $n$ are as previously defined; $R^9$ is methyl, ethyl, 2-hydroxyethyl, 2-methoxyethyl; and $R^{10}$ is alkyl or branched alkyl of 3-6 carbon atoms, or 4,4,4-trifluorobutyl. This method essentially involves successively alkylating in any order di-tert.-butyl malonate with halo-substituted esters of the formula

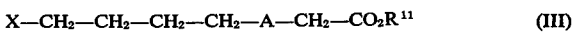 (III)

wherein A is as previously defined, X is halogen (chlorine, bromine, or iodine), and $R^{11}$ is straight chain lower alkyl (ethyl or methyl), and

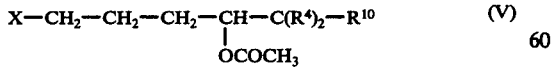 (V)

wherein X is halogen and $R^4$ and $R^{10}$ are as previously defined,
and heating the resulting appropriately substituted malonic ester in the presence of a strong acid to eliminate isobutylene and carbon dioxide with production of the key intermediate VII of the formula

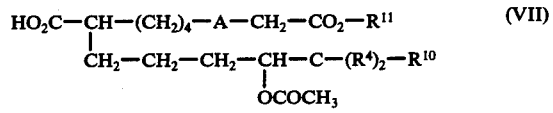 (VII)

This carboxy diester VII is then treated with red mercuric oxide and bromine to effect replacement of the carboxy function with bromine. The resulting bromo compound is then treated with a lower alkyl mercaptan to displace the bromo substituent and produce a derivative of compound II which has the hydroxyl and carboxy functions protected as esters. This alkylthio compound is then subjected to basic hydrolysis to produce one of the preferred sub-groups of compounds of this invention of formula II wherein $n = 0$. This thia compound II is then converted by oxidation to the corresponding oxothia compound II of this invention wherein $n = 1$ or the dioxothia compound II wherein $n = 2$. A detailed description of this method follows. (1) Di-tert.-butyl malonate is converted to its anion by a suitable base (sodium hydride) preferably in aprotic solvent or solvent system (dimethylformamide or dimethylformamide-benzene) and then alkylated with III at a temperature of from 60°–120° C. for a period of from 12–72 hours $$X-CH_2CH_2CH_2CH_2ACH_2CO_2R^{11} \quad (III)$$

wherein A is as previously defined, X is halogen (chlorine, bromine, or iodine), and $R^{11}$ is straight chain lower alkyl (ethyl or methyl).

 (III)

 (IV)

(2) The malonic ester product of Step (1) (IV) is converted to the anion similarly and alkylated with V

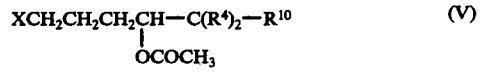 (V)

wherein X is halogen, and $R^4$ and $R^{10}$ are as previously defined.

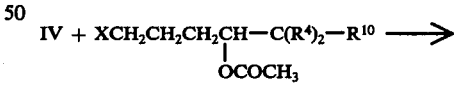

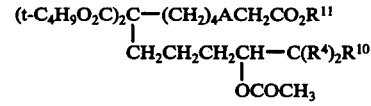 (VI)

Note: order of alkylation can be reversed, i.e., V can be used first and then III. (3) VI is heated with a catalytic quantity of strong acid (p-toluenesulfonic acid or $H_2SO_4$) in an inert solvent, preferably a higher boiling solvent such as toluene or xylene, to effect elimination of isobutylene and decarboxylation of resulting malonic acid.

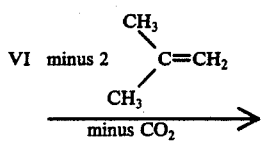

VI minus 2 $\underset{\text{minus CO}_2}{\overset{\text{CH}_3}{\underset{\text{CH}_3}{\diagdown}}}\text{C}=\text{CH}_2 \longrightarrow$

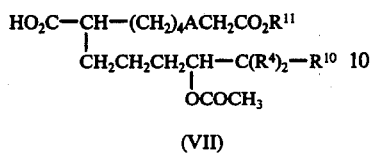

(VII)

(4) VII is treated with red mercuric oxide and bromine (Hunsdiecker reaction) in carbon tetrachloride to give the bromo compound VIII.

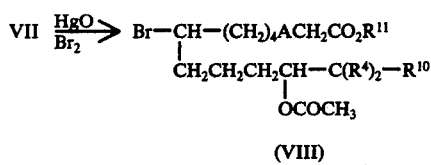

(VIII)

(5) VIII is reacted with an alkali metal salt, e.g., a sodium salt of a mercaptan $R^9SH$ ($R^9$ as previously defined) in a solvent such as ethanol or methanol to give IX.

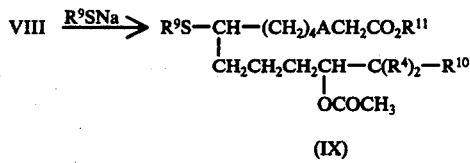

(IX)

(6) IX is subjected to basic hydrolysis (dilute NaOH or KOH in methanol, ethanol or tetrahydrofuran) to remove protecting ester functions:

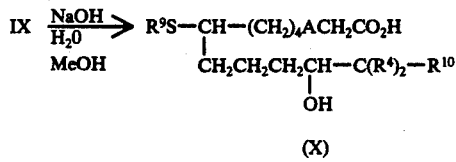

(X)

(7a) X can be oxidized with sodium metaperiodate (in dilute $NaHCO_3$ solution) to give the sulfoxide products of this invention ($n = 1$) (XI):

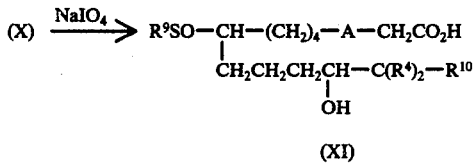

(XI)

(7b) Either X or XI can be oxidized with hydrogen peroxide (30% $H_2O_2$ in water) in a suitable solvent (ethanol, isoPrOH, acetic acid) to give the sulfone products of this invention (n = 2) (XII):

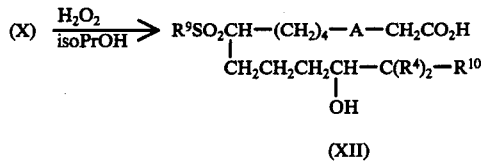

(XII)

Typical of the compounds which may be prepared by this method are
8-methylthio-12-hydroxyheptanoic acid
8-methylsulfinyl-12-hydroxyheptadecanoic acid
8-methylsulfonyl-12-hydroxyheptadecanoic acid
8-(2-hydroxyethylsulfonyl)-12-hydroxyheptadecanoic acid
8-(2-methoxyethylsulfonyl)-12-hydroxyheptadecanoic acid The second method of synthesis of compounds of this invention is especially useful for the preparation of another preferred sub-group of compounds of formula XIII

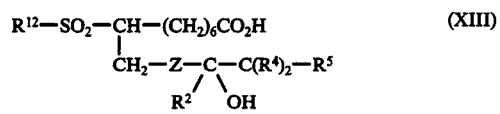

(XIII)

wherein Z, $R^2$, $R^4$ and $R^5$ are as defined above, and $R^{12}$ is methyl or ethyl. In this method, an alkyl sulfonyl derivative of an azelaic acid diester is alkylated under basic conditions with a substituted halo ester or ether and the alkylated product heated to effect decarbalkoxylation of the intermediate and resultant production of a derivative of compound XIII in which the hydroxyl substituent is protected by an alkanoyl or benzyl group and the carboxy function by esterification. Mild basic hydrolysis and/or hydrogenolysis of the benzyl group, if present, produces the compounds of sub-group XIII. A detailed description of this method follows. (1) Dimethyl (or diethyl) 2-bromoazelate is made to react with the sodium salt of a mercaptan $R^{12}SH$ to give the sulfide XIV. The reaction is run in an anhydrous alcoholic solvent, e.g., methanol, ethanol or propanol. The sodium salt of mercaptan $R^{12}SH$ is prepared by adding sodium methoxide or ethoxide to the alcohol solvent and then adding $R^9SH$ wherein $R^9$ is as previously defined.

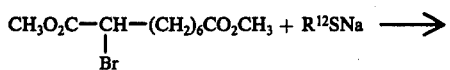

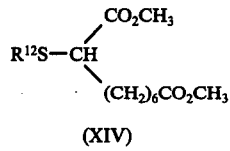

(XIV)

2. Sulfide XIV is oxidized with hydrogen peroxide (30% aqueous $H_2O_2$) to give sulfone XV. This oxidation can be run in an alcohol (methanol, ethanol, isoPrOH) or acetic acid. A small amount of ammonium molybdate catalyst is beneficial.

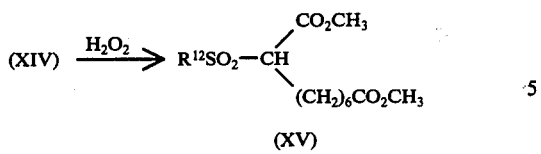

(XV)

3. The sulfone is converted to its anion with a suitable base (NaH) in aprotic solvent (dimethylformamide or dimethylformamide-benzene) and alkylated with either

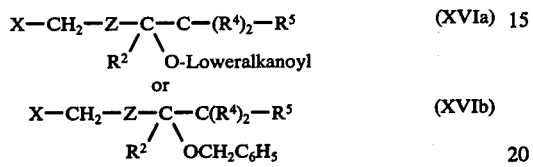

wherein X is halogen (bromine, chlorine, or iodine) and $R^2$, $R^4$ and $R^5$ are as previously defined.

Reaction:

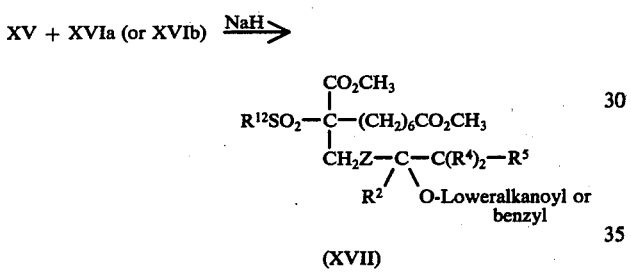

(XVII)

4. The decarbalkoxylation of XVII is carried out by heating XVII in dimethyl sulfoxide with about 2 molar equivalents of water and 1 molar equivalent of sodium chloride at 130°–160° C. for 3–10 hours.

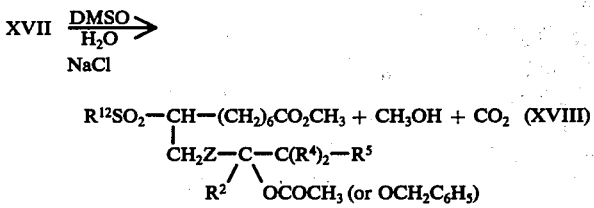

5. If the hydroxyl group of XVIII is protected by the acetyl group ($OCOCH_3$) mild basic hydrolysis (NaOH, and $H_2O$ in methanol, ethanol or tetrahydrofuran) gives the products of the invention XIII.

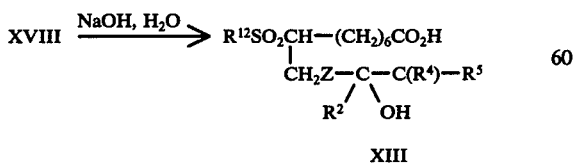

If the hydroxyl group of XVIII is protected by a benzyl group ($OCH_2C_6H_5$), mild basic hydrolysis gives the compounds XIX.

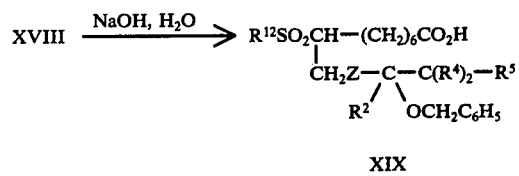

XIX

The benzyl group is removed from XIX by hydrogenolysis over a palladium catalyst in a lower alkanol or lower aliphatic carboxylic acid ester solvent, e.g., ethanol or ethyl acetate. The products of the invention XIII are obtained.

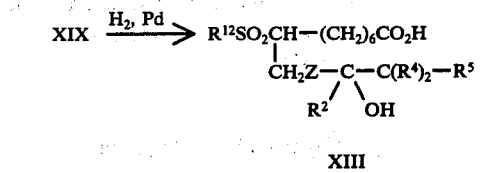

XIII

It is to be recognized that hydrogenolysis of the benzyl protecting group will at the same time result in reduction of unsaturated bonds in Z or $R^5$.

The third method of synthesis of this invention is especially useful for the preparation of still another preferred sub-group of compounds of formula XX:

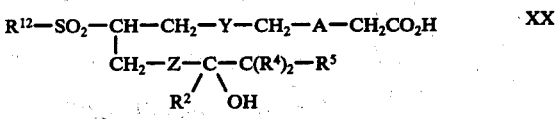

wherein all symbols are as previously defined. In this method, an alkyl sulfonyl derivative of ethyl acetate is successively alkylated in the presence of a strong base with two selected bromo esters and the resulting product decarbalkoxylated by heating in a solvent. Mild basic hydrolysis gives the compounds of the present invention. A detailed description of the method follows:

1. Ethyl methylsulfonylacetate or ethyl ethylsulfonylacetate ($R^{12}SO_2CH_2CO_2C_2H_5$) are converted to their anions ($R^{12}SO_2^-CH-CO_2C_2H_5$) with a suitable strong base (sodium hydride) in aprotic solvent (dimethylformamide, dimethylformamide-benzene) and alkylated with $$X-CH_2-Y-CH_2A-CH_2CO_2R^{11} \qquad XXI$$

wherein X is halogen, and Y, A and $R^{11}$ are as previously defined.

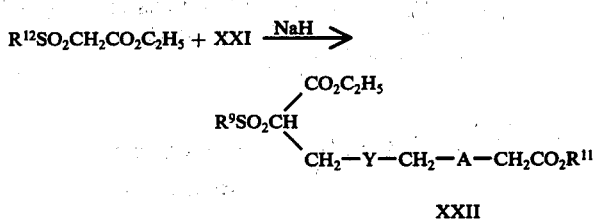

XXII

2. XXII is similarly converted to anion by strong base and alkylated with

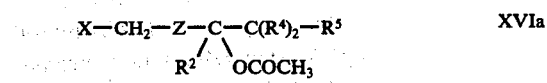

wherein X is halogen and the other symbols are as previously defined.

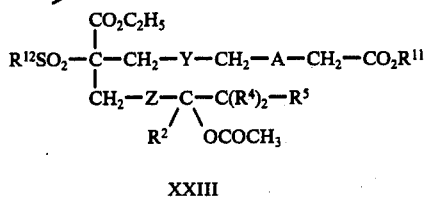

XXIII

3. The decarbalkoxylation of XXIII is carried out by heating XXIII in dimethylsulfoxide with about 2 molar equivalents of water and 1 molar equivalent of NaCl at 130°–160° C. for 3–5 hours.

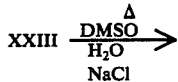

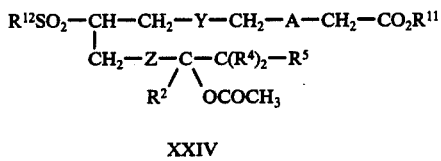

XXIV

4. Compounds XXIV are subjected to mild basic hydrolysis (NaOH or KOH in aqueous methanol, ethanol or tetrahydrofuran) at 25° C. to 65° C. for 24 to 64 hours to give the products of the invention XX.

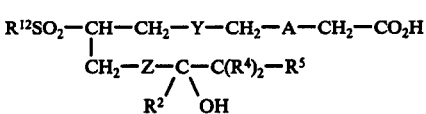

XX

It is frequently advantageous from a therapeutic standpoint to prepare compounds of this invention (formula I) in which the asymmetric carbon atom bearing $R^2$ and $OR^3$ is exclusively in the R or S configuration.

The compounds of the instant invention in which the $C_{12}$-carbon is in the S-configuration have greater biological activity than those in which the $C_{12}$-carbon is in the R-configuration. The relative biopotency is readily determined in any particular instance by the use of the in vitro or in vivo assays referred to hereinabove.

In our series of 9-thia-, 9-oxothia-, and 9-dioxothia-11,12-seco-prostaglandins, compounds exclusively R or S at this center can be produced by employing, in any of the three fundamental methods, intermediates V, XVIa or XVIb, which are optically active, i.e., resolved into their R and S stereoisomeric forms.

We have found it particularly advantageous to employ an optically-active reagent XVIac,

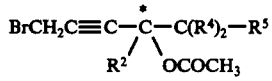

XVIac in which $R^2$, $R^4$, and $R^5$ are as previously defined, and the carbon atom marked with an asterisk is exclusively in either the R or S configuration.

For example, the use of XVIac in method III gives intermediates XXIIIa

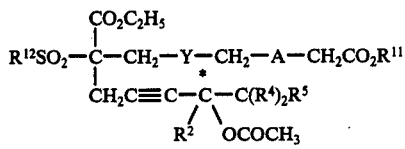

XXIIIa which are decarbalkoxylated and subsequently hydrolyzed in base to yield the optically active products of the invention XXa in which the carbon marked

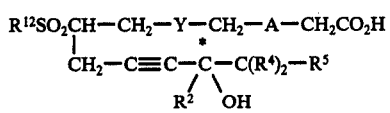

XXa with an asterisk is exclusively in either the R or S configuration.

Catalytic hydrogenation of products XXa gives further compounds of the invention, XXb, with the asterisked carbon exclusively in either the R or S configuration:

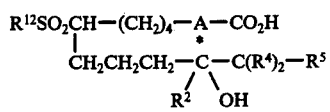

XXb

DERIVATIZATION OF PRODUCTS FROM THE MAJOR PROCESSES

The directly obtained products of Methods I, II and III described supra can be derivatized in a variety of ways to yield other products of formula I.

1. The fundamental processes yield compounds where R is carboxy. To obtain carboxy salts the acid products are dissolved in a solvent such as ethanol, methanol, glyme and the like and the resulting solution treated with an appropriate alkali or alkaline earth hydroxide or alkoxide to yield the metal salt, or with an equivalent quantity of ammonia, amine or quaternary ammonium hydroxide to yield the amine salt. In each instance, the salt either separates from the solution and may be collected by filtration or, when the salt is soluble, it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine or a quaternary ammonium hydroxide.

To obtain carboxy esters (i.e., compounds where R is alkoxycarbonyl) the acid products are treated in ether with an ethereal solution of the appropriate diazoalkane. For example, methyl esters are produced by reaction of the acid products with diazomethane. To obtain products where R is carbamoyl, substituted carbamoyl or carbazoyl the acid product is first converted to an active Woodward ester. For example, the acid product can be made to react with N-tert.-butyl-5-methylisoxazolium perchlorate in acetonitrile in the presence of a base such as triethylamine to yield an active ester in which R is

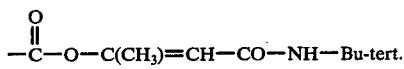

Active esters of this type can be reacted with ammonia to yield products of formula I where R is carbamoyl, with primary or secondary amines or di-lower-alkylaminoalkylamines to yield products where R is substituted carbamoyl, i.e., —CONR$^7$R$^8$, and with hydrazine to yield products where R is carbazoyl.

2. The fundamental processes yield products where R$^3$ is hydrogen. In compounds containing no additional hydroxy group and in which R$^2$ is hydrogen, reaction with formic acid, acetic anhydride, propionic anhydride, butyric anhydride, isobutyric anhydride, valeric anhydride, pivalic anhydride and the like, without solvent and at temperatures from 25°–60° C., gives compounds wherein R$^3$ is formyl, acetyl, propionyl, butyryl, isobutyryl, valeryl, and pivaloyl, respectively.

3. Compounds of the invention in which Y and Z are unsaturated groups such as vinylene or ethynylene can be hydrogenated using a suitable catalyst to other compounds of the invention in which former ethynylene groups have been reduced to vinylene or ethylene, or former vinylene groups have been reduced to ethylene. Of particular interest is the hydrogenation of a Y ethynylene group over Lindlar catalyst to give Y cis-vinylene group and the reduction of a Z ethynylene group over palladium to give a Z ethylene group.

4. Compounds where R$^1$ is vinyl are prepared by the following scheme. The sulfide IX where R$^9$ is 2-hydroxyethyl (HOCH$_2$CH$_2$—) is treated with thionyl chloride to give a 2-chloroethylsulfide. This product is oxidized to a 2-chloroethylsulfone with hydrogen peroxide and treated with aqueous NaOH or KOH to effect elimination of HCl and hydrolysis of ester functions yielding the vinylsulfone product XXVI.

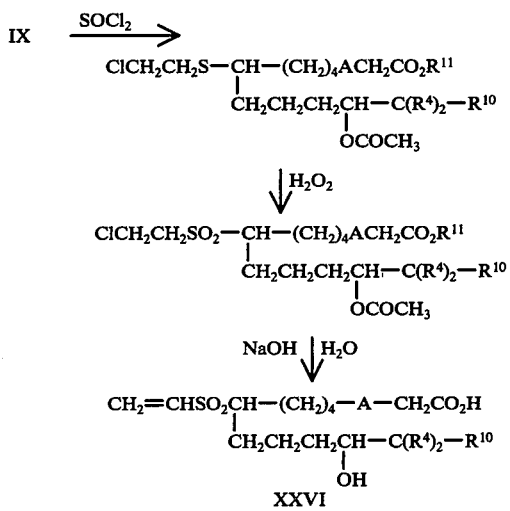

5. Compounds XIII or XX in which R$^2$ is hydrogen can be converted to the corresponding compounds where R$^2$ is methyl by the following efficient process. The compounds XIII or XX are treated with chromium trioxide to oxidize the secondary alcoholic functional group

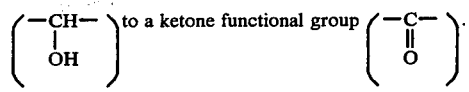

The resulting ketones are treated with from 2.5 to 4.0 molar equivalents of methylmagnesium bromide or iodide in a solvent, preferably tetrahydrofuran, to obtain products XIII or XX where R$^2$ is methyl.

PREPARATION OF REAGENTS

The reagents V which have the following general formula wherein X, R$^4$ and R$^{10}$ are as described above are prepared by the following process:

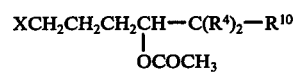

A Grignard reagent R$^{10}$–C(R$^4$)$_2$–MgBr(or I or Cl) is made to react in ether or tetrahydrofuran with a nitrile XCH$_2$CH$_2$CH$_2$CN. The immediately resulting imine complex is hydrolyzed in aqueous acidic solution to give a ketone of the formula XCH$_2$CH$_2$CH$_2$COC(R$^4$)$_2$–R$^{10}$. The ketone is reduced to the alcohol XCH$_2$CH$_2$CH$_2$CHOHC(R$^4$)$_2$–R$^{10}$ with sodium or potassium borohydride in a suitable solvent such as methanol, ethanol or digylme. Acetylation of the alcohol, preferably with acetic anhydride, gives the reagent V.

2. Reagents of the type XVIa in which X, R$^2$, R$^4$ and R$^5$ are as defined and Z is ethynylene are represented by the following formula and are designated XVIaa:

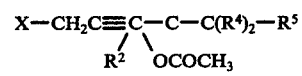

The reagents XVIaa are prepared by the following process:

Aldehydes (R$^2$ = H) or ketones (R$^2$ = methyl) of the formula R$^5$–C(R$^4$)$_2$–CO–R$^2$ are made to react with lithium acetylide or ethynylmagnesium bromide to give the alcohols HC≡C–C(R$^2$)OH–C(R$^4$)$_2$–R$^5$. The alcohols are acetylated preferably with acetic anhydride to give HC≡C–C(R$^2$)(OCOCH$_3$)–C(R$^4$)$_2$R$^5$. These compounds are treated with formaldehyde and dimethyl or diethylamine to give the amines (C$_2$H$_5$)$_2$NCH$_2$C≡C–C(R$^2$)(OCOCH$_3$)–C(R$^4$)$_2$–R$^5$. The amines are allowed to react with cyanogen bromide in ether to yield by displacement of (C$_2$H$_5$)$_2$N— the reagents XVIaa where X is bromide.

3. The reagents XVIba are those of type XVIb where Z is ethynylene:

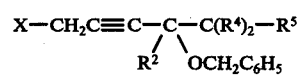

Reagents XVIba are prepared exactly analogously to reagents XVIaa except that the alcohols HC≡C–C(R$^2$)OH–C(R$^4$)$_2$–R$^5$ are benzylated (rather than acetylated) to give HC≡C–C(R$^2$)(OCH$_2$C$_6$H$_5$)–C(R$^4$)$_2$–R$^5$ by being treated with base (NaH) to give the alkoxide which is alkylated with benzyl chloride or benzyl bromide. Subsequent steps are analogous to those in the preparation of reagent XVIaa.

4. Reagents of the type XVI$a$ in which X, $R^2$, $R^4$ and $R^5$ are as defined and Z is vinylene are represented by the following formula and are designated XVI$ab$ $$X-CH_2-CH=CH-\underset{\underset{R^2}{\diagup}\overset{OCOCH_3}{\diagdown}}{C}-C(R^4)_2-R^5 \qquad \text{XVI}ab$$

Reagents XVI$ab$ are prepared as follows:

Grignard reagents $R^5C(R^4)_2MgBr$(or I or Cl) are made to react with crotonaldehyde ($R^2$ will equal hydrogen) or methyl propenyl ketone ($R^2$ will equal methyl) to give alcohols $$CH_3CH=CH-\underset{\underset{R^2}{\diagup}\overset{OH}{\diagdown}}{C}-C(R^4)_2-R^5.$$

The alcohols are acetylated preferably with acetic anhydride in pyridine to give the acetates $CH_3CH=CH-C(R^2)$ $(OCOCH_3)C(R^4)_2-R_5$. Reaction of the acetates with N-bromosuccinimide in carbon tetrachloride gives the reagents XVI$ab$ where X equals bromine.

If the alcohol products of the Grignard reaction are benzylated as described in (3) above the reagents XVI$bb$ are obtained:

$$XCH_2CH=CH-\underset{\underset{R^2}{\diagup}\overset{OCH_2C_6H_5}{\diagdown}}{C}-C(R^4)_2-R^5 \qquad \text{XVI}bb$$

5. Another particularly advantageous method is used to prepare reagents of type XVI$b$ (designated XVI$bc$) in which X is as described and Z is ethylene, $R^2$ and $R^4$ are hydrogen and $R^5$ is $OR^{5a}$.

$$XCH_2CH_2CH_2\underset{\underset{OCH_2C_6H_5}{|}}{CH}-CH_2-OR^{5a} \qquad \text{XVI}bc$$

Sodium alkoxides $R^{5a}ONa$ are reacted with bromoacetaldehyde diethyl (or dimethyl)acetal to give acetals which are hydrolyzed in aqueous acid to give the substituted acetaldehydes $R^{5a}OCH_2CHO$. The acetaldehydes are treated with allylmagnesium bromide or chloride to give the alcohols $CH_2=CH-CH_2-CH(OH)-CH_2-O-R^{5a}$. The alcohols are converted to their alkoxides with suitable base (NaH in dimethylformamide) and benzylated with benzyl choride or benzyl bromide. The resulting compounds are converted to the alcohols $$HOCH_2CH_2CH_2CH(OCH_2C_6H_5)CH_2O-R^{5a}$$

by the procedure of hydroboration (reaction with diborane in tetrahydrofuran followed by $H_2O_2$ oxidation in the presence of aqueous sodium hydroxide). The alcohols are converted to the corresponding tosylates by reaction with p-toluenesulfonyl chloride in pyridine and the tosylates heated with sodium iodide in acetone to give reagents XVI$bc$ where X equals iodine.

6. The optically active reagents XVI$ac$ are prepared:

$$BrCH_2C\overset{*}{\equiv}\underset{\underset{R^2}{\diagup}\overset{OCOCH_3}{\diagdown}}{C}-C(R^4)_2-R^5 \qquad \text{XVI}ac$$

are prepared by the method described in section (2) above for reagents XVI$aa$. Here aldehydes or ketones $R^5-C(R^4)_2-CO-R^2$ are reacted with lithium acetylide or ethynylmagnesium bromide to give the alcohols $HC\equiv C-C(R^2)OH-C(R^4)_2-R^5$. The alcohols are resolved into their optically active R and S enantiomers by standard methods of resolution (see Organic Reactions, Vol. II, Chapter 9, page 376, John Wiley and Sons, Inc., N.Y., N.Y., 1944). After resolution the enantiomers are carried separately through the remainder of the process described in section (2) above to yield reagents XVI$ac$.

EXAMPLE 1

Preparation of 8-methylthio-12-hydroxyheptadecanoic acid

Step A: Preparation of di-tert.-butyl (6-ethoxycarbonylhexyl)-malonate

A suspension of 57% sodium hydride in mineral oil (5.05 g. net weight, 0.21 mole) in a solvent mixture of benzene (95 ml.) and dimethylformamide (95 ml.) is treated, dropwise, over 30 minutes with di-tert.-butyl malonate (41.09 g., 0.19 mole). Stirring is continued for an additional 30 minutes. Then ethyl-7-bromoheptanoate (49.80 g., 0.21 mole) is added, dropwise, over 30 minutes, and the mixture is heated at 100° C. for 4-½ hours.

The cooled reaction mixture is treated with water (380 ml.) and the organic layer is separated. The aqueous layer is extracted with ether. The combined organic solutions are washed with saturated sodium chloride solution and then dried over anhydrous sodium sulfate. The solvents are removed under vacuum to give the title compound as a residual oil, yield 70.78 g.

Step B: Preparation of 1-chloro-4-acetoxynonane

Step B-1. Preparation of 1-chloro-4-nonanone

To the Grignard reagent prepared from a mixture of amyl bromide (226.59 g., 1.5 moles) and magnesium (36.48 g., 1.5 moles) in ether (100 ml.) is added, dropwise, during one hour, 4-chlorobutyronitrile (155.34 g., 1.5 moles). Stirring is continued for an additional 1 hour. The reaction mixture is poured into a mixture of finely crushed ice (1000 g.) and concentrated hydrochloric acid (750 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride and dried over anhydrous sodium sulfate. The solvent is removed under vacuum and the residual oil is distilled to give 69.0 g. (26%) of colorless oil, b.p. 115°–117°/14 mm.; pmr (CDCl$_3$) δ 0.90 (3H,t), 3.56 (2H,t,CH$_2$Cl).

Step B-2. Preparation of 1-chloro-4-nonanol

A suspension of sodium borohydride (6.62 g., 0.175 mole) and sodium hydroxide (1.3 g.) in ethanol (310 ml.) is treated, dropwise, over 1 hour with 1-chloro-4-nonanone (61.40 g., 0.349 mole) while the temperature is maintained at 45°–50° C. Stirring is continued for one hour, longer without external cooling.

The reaction mixture is acidified with concentrated hydrochloric acid to the Congo red endpoint and then the ethanol is removed under reduced pressure. The residue is treated with water (200 ml.) and the resulting oil is extracted with ether. The combined extracts are washed with saturated sodium chloride solution and dried over anhydrous sodium sulfate. The solvent is removed under vacuum to give the title compound as a light yellow residual oil, yield 58.85 g., ir (neat) 3400 cm$^{-1}$.

Step B-3. Preparation of 1-chloro-4-acetoxynonane

A mixture of 1-chloro-4-nonanol (111.99 g., 0.627 mole) and acetic anhydride (128.0 g., 1.254 moles) is heated on a steam bath for 1-½ hours.

The volatile materials are removed under reduced pressure and the residual oil is distilled to give 88.6 g. (64%) of colorless oil, b.p. 130°–133° C./14 mm., pmr (CDCl$_3$) δ 0.89 (3H, t), 2.02 (3H, s CH$_c$COO), 3.53 (2H,t CH$_2$Cl), 4.89 (1H,m). Anal. Calcd. for C$_{11}$H$_{21}$ClO$_2$: C, 59.85; H, 9.59. Found: C, 59.87; H, 9.67.

Step C. Preparation of di-tert.-butyl 2-(4-acetoxynonyl)-2-(6-ethoxycarbonylhexyl)malonate A suspension of 57% sodium hydride in mineral oil (5.05 g. net weight, 0.21 mole) in a solvent mixture of benzene (95 ml.) and dimethylformamide (95 ml.) is treated, dropwise, over 30 minutes, with di-tert.-butyl-(6-ethoxycarbonylhexyl)-malonate (69.70 g., 0.187 mole). Stirring is continued for an additional 2 hours. Then 1-chloro-4-acetoxynonane (46.35 g., 0.21 mole) is added, dropwise, over 30 minutes, and the mixture is heated at 100° C. for 42 hours.

The cooled reaction mixture is treated with water (380 ml.) and the organic layer is separated. The aqueous layer is extracted with ether. The combined organic solutions are washed with saturated sodium chloride solution and then dried over anhydrous sodium sulfate. The solvents are removed under vacuum to give the title compound as a residual oil, yield 104.12 g., p.m.r. (CDCl$_3$) δ 0.88 (3H,t), 1.45 (18H,s), 2.00 (3H, s CH$_3$COO), 4.12 (2H, q).

Step D. Preparation of ethyl 8-carboxy-12-acetoxyheptadecanoate

A mixture of di-tert.-butyl 2-(4-acetoxynonyl)-2-(6-ethoxycarbonylhexyl)malonate (104.12 g., 0.187 mole), p-toluenesulfonic acid monohydrate (3.30 g.) and toluene (330 ml.) is heated under reflux for 9-½ hours.

The cooled reaction mixture is washed well with saturated sodium chloride solution and then dried over anhydrous sodium sulfate. The solvent is removed under vacuum to give the title compound as a residual oil, yield 74.9 g. The oil is purified by column chromatography on silica gel with 2% methanol in chloroform as an eluent; pmr (CDCL$_3$) δ 0.88 (3H,t), 2.02 (3H, s CH$_3$COO), 4.12 (2H, q), 10.97 (1H, s COOH).

Anal. calcd. for C$_{22}$H$_{40}$O$_6$: C, 65.97; H, 10.07 Found: C, 66.24; H, 10.29

Step E. Preparation of ethyl 8-bromo-12-acetoxyheptadecanoate

A mixture of ethyl 8-carboxy-12-acetoxyheptadecanoate (31.5 g., 0.079 mole), red mercuric oxide (12.8 g., 0.059 mole), and carbon tetrachloride (200 ml.) is stirred at room temperature while bromine (12.6 g., 0.079 mole) is added dropwise during one hour. The resulting mixture is heated at reflux for one hour. The mixture is then cooled, filtered, washed with dilute hydrochloric acid, water and brine and dried over sodium sulfate. The solution is evaporated in vacuo to leave the product as a yellow residual weighing 24.5 g. The product is purified by chromatography on a column containing 250 g. of silica gel using chloroform as eluting solvent. There is obtained 14.4 g. of purified ethyl 8-bromo-12-acetoxyheptadecanoate, a yellow oil with Rf 0.49 on silica gel thin layer chromatography with chloroform elution. pmr (CDCl$_3$) δ 0.90 (3H,t); 2.03 (3H, s CH$_3$CO); 4.07 (1H, m HCBr); 4.13 (2H, q); 4.92 (1H, m HCO).

Step F. Preparation of 8-methylthio-12-hydroxyheptadecanoic acid

Gaseous methyl mercaptan is bubbled into a solution of sodium (3.7 g., 0.16 mole) in methanol (150 ml.) until 7.7 g. (0.16 mole) of the gas is absorbed. Ethyl 8-bromo-12-acetoxyheptadecanoate (17.8 g., 0.041 mole) is added and the resulting solution is heated at reflux for 4 hours. Then, a solution of 5.0 g. of sodium hydroxide in 50 ml. of water is added and reflux is continued for an additional hour. The solution is cooled, diluted with 500 ml. of water and extracted with ether. The aqueous solution is acidified with concentrated hydrochloric acid. The oily acid which separates is taken up in ether, washed with water and dried over sodium sulfate. The ether is evaporated to leave 12.5 g. of the crude product as a yellow viscous oil. Purification is effected by chromatography on a column containing 250 g. of silica gel using 2% methanol in chloroform as eluant. There is obtained 7.0 g. (51%) of 8-methylthio-12-hydroxyheptadecanoic acid as a light yellow viscous oil; pmr (CDCl$_3$) δ 0.90 (3H,t); 2.07 (3H, s CH$_3$S); 3.64 (1H, m HCO). Anal. Calcd. for C$_{18}$H$_{36}$O$_3$S: C, 65.01; H, 10.91 Found: C, 65.40; H, 10.98

EXAMPLE 2

Preparation of 8-methylsulfonyl-12-hydroxyheptadecanoic acid

A mixture of 8-methylthio-12-hydroxyheptadecanoic acid (Ex. 1) (3.0 g., 0.009 mole) and ammonium molybdate (0.10 g.) in isopropyl alcohol (10 ml.) is stirred and cooled in an ice bath while 30% aqueous hydrogen peroxide (5 ml., 0.044 mole) is added dropwise at such a rate to keep the temperature below 20° C. The mixture is then stirred 16 hours at 25° C. It is diluted with water (75 ml.) and the product extracted into chloroform, washed with brine and dried over sodium sulfate. The chloroform is evaporated in vacuo and the crude product purified by chromatography on silica gel with benzene-dioxane-acetic acid, 90:30:1, elution. The title compound is obtained as a yellowish viscous oil weighing 1.85 g. (56% yield).

Anal. Calcd. for C$_{18}$H$_{36}$O$_5$S: C, 59.30; H, 9.96; S, 8.80 Found: C, 58.95; H, 9.78; S, 8.47

EXAMPLE 3

Preparation of 8-methylsulfonyl-12-hydroxyheptadecanoic acid

Step A. Preparation of dimethyl 2-methylthioazelate

Methyl mercaptan (excess) is passed into a rapidly stirred solution of sodium methoxide (13.5 g., 0.25 mole) in dry methanol (200 ml.) at 0° C. to generate sodium methylmercaptide. The resulting solution is treated with dimethyl 2-bromoazelate (55.0 g., 0.186 mole), then stirred and heated at reflux under nitrogen for 5 hours. The reaction solution is concentrated in vacuo, diluted with ether and filtered. The filtrate is washed with water (until the washings are neutral), dried over sodium sulfate and distilled providing the title compound as a colorless liquid (28.4 g., 58%), bp 0.2 mm 128°–138° C.; pmr (CDCl$_3$) δ 2.10 (s, 3H), 2.31 (t,2H), 3.20 (t,H), 3.63 (s,3H) and 3.71 (s, 3H).

Anal. Calcd. for C$_{12}$H$_{22}$O$_4$S: C, 54.93; H, 8.45 Found: C, 55.03; H, 8.54

Step B-1. Preparation of dimethyl 2-methylsulfonylazelate

30% Hydrogen peroxide (28 g., ~ 0.25 mole) is added dropwise to a cooled (~10° C.), stirred mixture of dimethyl 2-mercaptoazelate (26.2 g., 0.01 mole) and ammonium molybdate (0.3 g., catalyst) in methanol (20 ml.) at such a rate as to maintain an internal temperature less than 30° C. The resulting reaction mixture is stirred at ambient temperature for 16 hours, then diluted with water (150 ml.) and filtered to yield the title compound as a white, crystalline solid (26.2 g., 89%), m.p. 47°–8° C. Recrystallization from ether at −10° C. provides an analytical sample as colorless needles, m.p. 50°–50.5° C.; pmr (CDCl$_3$) δ 3.0 (s, 3H), 3.63 (s, 3H), 3.72 (t, H) and 3.82 (s, 3H).

Anal. calcd. for C$_{12}$H$_{22}$O$_6$S: C, 48.97; H, 7.53 Found: C, 49.16; H, 7.77

Step B-2. Preparation of 1-iodo-4-acetoxynonane

A mixture of 1-chloro-4-acetoxynonane (Ex. 1, Step B-3) (35.3 g., 0.16 mole) and sodium iodide (120 g., 0.8 mole) in acetone (350 ml.) is stirred and heated at reflux with exclusion for light for 10 hours. The resulting suspension is filtered and the collected sodium chloride washed with acetone. The combined filtrate and washings are evaporated in vacuo leaving a residual mass which is partitioned between ether and water. The organic extract is washed with dilute aqueous sodium thiosulfate and water, dried over sodium sulfate and evaporated in vacuo providing the title compound as a colorless liquid (48.7 g., 98%), pmr (CDCl$_3$) δ 2.0 (s, 3H), 3.18 (t, 2H) and 4.98 (m, H).

Step C. Preparation of methyl 8-methoxycarbonyl-8-methylsulfonyl-12-acetoxyheptadecanoate A suspension of 57% sodium hydride/mineral oil (3.84 g., 0.091 mole) is washed by decantation with petroleum ether to remove the mineral oil. The residual solid is suspended in dry dimethylformamide (100 ml.) and treated with a solution of dimethyl-2-methylsulfonylazelate (23.5 g., 0.08 mole) in dry dimethylformamide (60 ml.) added dropwise at ambient temperature under a nitrogen atmosphere. The resulting solution is stirred for 1 hour at room temperature, cooled to ~ 10° C., and treated with 1-iodo-4-acetoxynonane (30 g., 0.096 mole) added at such a rate as to maintain an internal temperature less than 35° C. After 19 hours at ambient temperature, the reaction mixture is filtered. Collected sodium iodide (17.1 g.) is washed with ether. The combined filtrate and washings are concentrated in vacuo at ~ 100° C. yielding a residual oil which is partitioned between ether and dilute hydrochloric acid. The organic extract is washed with water and saturated brine, dried over magnesium sulfate and evaporated in vacuo leaving the title compound as a viscous oil (37.7 g., 98%), pmr (CDCl$_3$) δ 2.0 (s, 3H), 3.0 (s, 3H), 3.65 (s, 3H), 3.81 (s, 3H) and 4.9 (b, H).

Step D. Preparation of methyl 8-methylsulfonyl-12-acetoxyheptadecanoate

A mixture of methyl 8-methoxycarbonyl-8-methylsulfonyl-12acetoxyheptadecanoate (36.7 g., 0.077 mole), sodium chloride (4.68 g., 0.08 mole), water (1 ml.) and dimethylsulfoxide (60 ml.) is heated in a bath maintained at 185° C. under nitrogen for 5 hours. The resulting reaction mixture is concentrated in vacuo at 100° C. providing an oily residue which is diluted with water. The aqueous mixture is acidified to Congo Red with 6N hydrochloric acid and extracted with ether. The organic extract is washed with water, dried over magnesium sulfate, filtered and evaporated in vacuo leaving the title compound as a viscous oil (31 g., 95%), pmr (CDCl$_3$) δ 2.0 (s, 3H), 2.82 (s, 3H), 3.63 (s, 3H) and 4.9 (b, H).

Step E. Preparation of 8-methylsulfonyl-12-hydroxyheptadecanoic acid

A solution of methyl 8-methylsulfonyl-12-acetoxyheptadecanoate (29.4 g., 0.07 mole) and 20% aqueous sodium hydroxide (70 ml.) in methanol (70 ml.) is stirred at room temperature for 17 hours. The resulting solution is evaporated in vacuo at ~ 100° C. to an oily residue which is dissolved in water. The aqueous solution is extracted with ether and the organic extract discarded. Then, the aqueous phase is acidified to Congo Red with 6N hydrochloric acid and extracted with ether. The organic extract is washed with water, dried over magnesium sulfate, filtered and concentrated in vacuo at ~ 100° C. providing crude title compound as a viscous oil (23.6 g., 93%).

The viscous oil is applied to a silica gel column (700 g., 0.063–0.2 mm., E. Merck, Darmstadt) with benzene-dioxane-acetic acid (90:15:1; v:v:v). Elution with the same mixture provides the pure title compound as a colorless, viscous oil (16.5, 65%), pmr (CDCl$_3$) δ 2.82 (s, 3H), 2.82 (b, H), 3.63 (b, H) and 7.2 (s, 2H, exchangeable); pk$_a$ 5.20 (water).

Anal. calcd. for C$_{18}$H$_{36}$O$_5$S: C, 59.30; H, 9.96; S, 8.80 Found: C, 59.03; H, 9.60; S, 8.78

EXAMPLE 4

Preparation of 8-methylsulfinyl-12-hydroxyheptadecanoic acid

8-Methylthio-12-hydroxyheptadecanoic acid (Ex. 1) (6.7 g., 0.0202 mole) is dissolved in a solution of sodium hydroxide (1.0 g., 0.025 mole) in water (80 ml.). Sodium metaperiodate (4.7 g., 0.022 mole) is added and the resulting mixture is stirred at room temperature overnight (17 hours). The solids present are then filtered off and the filtrate is acidified with dilute hydrochloric acid to liberate the oily acid product. The oil is taken up in ether, washed with water and dried over sodium sulfate. The ether is evaporated in vacuo to leave the crude 8-methylsulfinyl-12-hydroxy-heptadecanoic acid as a viscous yellowish oil weighing 5.8 g. Purification is effected by chromatography on a column containing 125 g. of silica gel using 4% methanol in chloroform as eluant. There is obtained 2.2 g. of pure 8-methylsulfinyl-12-hydroxyheptadecanoic acid, a colorless viscous oil with Rf 0.14 on silica gel thin layer chromatograms with chloroform-methanol-acetic acid 96:3:1 as eluant; pmr (CDCl$_3$) δ 0.90 (3H, t); 2.50 (3H, s CH$_3$SO); 3.64 (1H, m HCO).

Anal. Calcd. for C$_{18}$H$_{36}$O$_4$S: C, 62.03; H, 10.41. Found: C, 61.72; H, 10.26.

EXAMPLE 5

Preparation of 8-ethylsulfonyl-12-hydroxyheptadecanoic acid

Step A. Preparation of 8-ethylthio-12-hydroxyheptadecanoic acid

This product is obtained by using the same procedure described in Example 1, Step F but substituting ethyl mercaptan for the methyl mercaptan of the example. 8-Ethylthio-12-hydroxy-heptadecanoic acid is obtained as a colorless viscous oil after purification by chromatography on silica gel.

Step B. Preparation of 8-ethylsulfonyl-12-hydroxyheptadecanoic acid

This product is obtained by using the procedure described in Example 2 but substituting 8-ethylthio-12-hydroxyheptadecanoic acid for the 8-methylthio-12-hydroxyheptanoic acid employed in the example. 8-Ethylsulfonyl-12-hydroxyheptadecanoic acid is obtained as a colorless, very viscous oil after purification by chromatography on silica gel with the elution system described in Example 2.

EXAMPLE 6

Preparation of 8-(2-hydroxyethylthio)-12-hydroxyheptadecanoic acid

2-Mercaptoethanol (15.6 g., 0.2 mole) is dissolved in a solution of sodium (4.6 g., 0.2 mole) in methanol (200 ml.). Ethyl 8-bromo-12-acetoxyheptadecanoate (Example 1, Step E) (22.3 g., 0.051 mole) is added and the resulting solution is heated at reflux for 4.5 hours. Then, a solution of 8 g. of sodium hydroxide in 40 ml. of water is added and reflux is continued for an additional hour. Most of the methanol is removed by evaporation in vacuo; the residue is diluted with 300 ml. of water and extracted with ether. The aqueous solution is acidified with concentrated hydrochloric acid. The oily acid that separates is taken up in ether, washed with water, and dried over sodium sulfate. The ether is evaporated to leave 18 g. of the crude product as a viscous yellow oil. Purification is effected by chromatography on a column containing 250 g. of silica gel using 3% methanol in chloroform as eluant. There is obtained 6.3 g. of pure 8-(2-hydroxyethylthio)-12-hydroxyheptadecanoic acid, a colorless viscous oil with Rf 0.24 on the silica gel thin layer chromatogram with chloroform-methanol-acetic acid 96:3:1 as eluant; pmr (CDCl$_3$) δ 0.90 (3H, t); 2.34 (2H, t $\underline{CH_2}CO_2H$); 2.72 (2H, t CH$_2$S); 3.74 (3H, combined t and m $\underline{CH_2}OH$, $\underline{H}COH$); 5.40 (3H, s COOH and OH).

Anal. calcd. for C$_{19}$H$_{38}$O$_4$S: C, 62.94; H, 10.56. Found: C, 62.59; H, 10.57.

EXAMPLE 7

Preparation of 8-(2-hydroxyethylsulfonyl)-12-hydroxyheptadecanoic acid

A solution consisting of 8-(2-hydroxyethylthio)-12-hydroxyheptadecanoic acid (6.0 g., 0.0165 mole), 30% aqueous hydrogen peroxide (8 ml.) and isopropyl alcohol (40 ml.) is allowed to stand 18 hours at 25° C. The solution is then diluted with 140 ml. of water. The oily product is taken up in ether, washed with water and dried over sodium sulfate. The ether is evaporated to leave 6.8 g. of crude product as a viscous yellow oil. The product is purified by chromatography on a column containing 125 g. of silica gel using 3% methanol in chloroform as eluant. There is obtained 2.4 g. of 8-(2-hydroxyethylsulfonyl)-12-hydroxyheptadecanoic acid, a colorless viscous oil with Rf 0.18 on the silica gel thin layer chromatogram with chloroform-methanol-acetic acid 95:4:1 as eluant; pmr (CDCl$_3$) δ 0.90 (3H, t); 2.37 (2H, t $\underline{CH_2}CO_2H$); 3.21 (2H, t CH$_2$SO$_2$); 3.66 (1H, m HCO); 4.14(2H, t $\underline{CH_2}OH$); 5.52 (3H, s COOH and OH).

Anal. calcd. for C$_{19}$H$_{38}$O$_6$S: C, 57.84; H, 9.71; S, 8.13. Found: C, 58.29; H, 10.03; S, 8.12.

EXAMPLE 8

Preparation of 8-vinylsulfonyl-12-hydroxyheptadecanoic acid

Step A. Preparation of ethyl 8-(2-hydroxyethylthio)-12-acetoxyheptadecanoate 2-Mercaptoethanol (31.2 g., 0.4 mole) is dissolved in a solution of sodium (9.2 g., 0.4 mole) in methanol (300 ml.). Ethyl 8-bromo-12-acetoxy-heptadecanoate (Example 1, Step E) (43.5 g., 0.1 mole) is added and the resulting solution is heated at reflux for 5 hours. Most of the methanol is then removed by evaporation in vacuo. Water (350 ml.) is added to the residue and the oily product taken up in ether, washed with water and brine and dried over sodium sulfate. Evaporation of the ether leaves the title compound as a yellow residual oil which is used in the next step without further purification.

Step B. Preparation of ethyl 8-(2-chloroethylthio)-12-acetoxyheptadecanoate Thionyl chloride (13.1 g., 0.11 mole) is added dropwise with stirring to a solution of ethyl 8-(2-hydroxyethylthio)-12 -acetoxyheptadecanoate (43.2 g., 0.10 mole) in benzene (150 ml.). The solution is heated at reflux for 2 hours. Then, the solvent and excess thionyl chloride are removed by evaporation in vacuo to leave the title compound as an orange yellow residual oil.

Step C. Preparation of ethyl 8-(2-chloroethylsulfonyl)-12-acetoxyheptadecanoate A solution of ethyl 8-(2-chloroethylthio)-12-acetoxyheptadecanoate (45.1 g., 0.1 mole) and 30% aqueous hydrogen peroxide (50 ml.) in acetic acid (225 ml.) is allowed to stand 20 hours at 25° C. The solution is diluted with 600 ml. of water. The oily product is taken up in ether, washed with dilute sodium bicarbonate solution and four portions of water and dried over sodium sulfate. Evaporation of the ether in vacuo leaves the title compound as a light yellow viscous oil.

Step D. Preparation of 8-vinylsulfonyl-12-hydroxyheptadecanoic acid

A mixture of ethyl 8-(2-chloroethylsulfonyl)-12-acetoxyheptadecanoate (43.5 g., 0.09 mole), sodium hydroxide (14.4 g., 0.36 mole), water (150 ml.) and tetrahydrofuran (600 ml.) is stirred at 25° C. for 24 hours. Most of the tetrahydrofuran is removed by evaporation in vacuo keeping the temperature of the evaporating solution at 30° C. or below. The residue is diluted with water (300 ml.) and extracted with ether. The aqueous solution is acidified with dilute hydrochloric acid. The oily product is taken up in ether, washed with water and dried over sodium sulfate. The ether is evaporated to leave the product as a yellowish, very viscous oil. Purification is effected by column chromatography on silica gel with benzene-dioxane as eluting solvent mixture. The title compound is obtained as a colorless viscous oil.

EXAMPLE 9

Preparation of
5-methylsulfonyl-9-hydroxytetradecyloxyacetic acid

Step A. Ethyl 4-bromobutoxyacetate

Sodium hydride (9.0 g., 0.375 mole) is suspended in 1,2-dimethoxyethane. The mixture is stirred and cooled in an ice bath while ethyl glycollate (39.0 g., 0.375 mole) is added dropwise during one hour. 1,4-Dibromobutane (108 g., 0.5 mole) is added all at once to the resulting thick suspension. The mixture is warmed gently to initiate a strongly exothermic reaction; then the mixture is heated 3hours on the steam bath. The mixture is poured into cold water. The heavy oil layer is taken up in ether, washed with three portions of water, and dried over sodium sulfate.

Evaporation of the ether and distillation of the residual oil yields 21.3 g. (24%) of ethyl 4-bromobutoxyacetate, a colorless oil, b.p. 99°–103° C./0.2 mm.

Step B. Preparation of di-tert.-butyl [4-(ethoxycarbonylmethoxy)-butyl]malonate This compound is prepared essentially by the method described in Example 1, Step A except that the ethyl 7-bromoheptanoate of the example is replaced by ethyl 4-bromobutoxyacetate. The title compound is obtained as a residual oil.

Step C. Preparation of di-tert.-butyl 2-(4-acetoxynonyl)-2-[4-(ethoxycarbonylmethoxy)-butyl]malonate This compound is prepared essentially by the method described in Example 1, Step C except that the di-tert.-butyl (6-ethoxycarbonylhexyl)-malonate of the example is replaced by di-tert.-butyl [4-(ethoxycarbonyl-methoxy)-butyl]malonate. The title compound is obtained as a residual oil.

Step D. Preparation of ethyl 5-carboxy-9-acetoxytetradecyloxyacetate

This compound is prepared essentially by the method described in Example 1, Step D except that the di-tert.-butyl 2-(4-acetoxynonyl)-2-(6-ethoxycarbonylhexyl)-malonate of the example is replaced by di-tert.-butyl 2-(4-acetoxynonyl)-2-[4-(ethoxycarbonylmethoxy)-butyl]-malonate. The title compound is purified by column chromatography on silica gel.

Step E. Preparation of ethyl 5-bromo-9-acetoxy-tetradecyloxyacetate

This compound is prepared essentially by the method described in Example 1, Step E except that the ethyl 8-carboxy-12-acetoxyheptadecanoate of the example is replaced by ethyl-5-carboxy-9-acetoxytetradecyloxyacetate. The title compound is purified by column chromatography on silica gel.

Step F. Preparation of 5-methylthio-9-hydroxytetradecyloxyacetic acid

This compound is prepared essentially by the method described in Example 1, Step F except that the ethyl 8-bromo-12-acetoxy-heptadecanoate of the example is replaced by ethyl 5-bromo-9-acetoxytetradecyloxyacetate. The title compound is purified by column chromatography on silica gel.

Step G. Preparation of 5-methylsulfonyl-9-hydroxytetradecyloxyacetic acid

This compound is prepared essentially by the method described in Example 2 except that the 8-methylthio-12-hydroxyheptadecanoic acid of Example 2 is replaced by 5-methylthio-9-hydroxytetradecyloxyacetic acid. The product is purified by chromatography on silica gel and is obtained as a very viscous yellowish oil.

EXAMPLE 10

Preparation of
8-methylsulfonyl-12-hydroxy-5-heptadecynoic acid

Step A. Ethyl 2-(6-methoxycarbonyl-2-hexyn-1-yl)-2-(methylsulfonyl)acetate

A suspension of 57% sodium hydride in mineral oil (5.05 g. net weight, 0.21 mole) in a solvent mixture of benzene (95 ml.) and dimethylformamide (95 ml.) is treated, dropwise over 30 minutes, with ethyl methylsulfonylacetate (33.2 g., 0.20 mole). Stirring is continued for an additional 30 minutes. Then methyl 7-bromo-5-heptynoate (43.8 g., 0.20 mole) is added dropwise during 30 minutes and the mixture is heated at 80° C. for 1.5 hours.

The cooled mixture is treated with water and the organic layer separated, washed with water and brine and dried over sodium sulfate. The solvent is evaporated in vacuo to leave the title compound as a yellow residual oil.

Step B. Preparation of ethyl 2-(6-methoxycarbonyl-2-hexyn-1-yl)-2-(4-acetoxynonyl)-2-(methylsulfonyl)acetate This compound is prepared essentially by the method described in Example 1, Step C, except that the di-tert.-butyl (6-ethoxycarbonylhexyl)malonate of the example is replaced by ethyl 2-(6-methoxycarbonyl-2-hexyn-1-yl)-2-(methylsulfonyl)acetate.

Step C. Preparation of methyl 8-methylsulfonyl-12-acetoxy-5-heptadecynoate

A solution of ethyl 2-(6-methoxycarbonyl-2-hexyn-1-yl)-2-(4-acetoxynonyl)-2-(methylsulfonyl)-acetate (48.8 g., 0.1 mole), water (3.6 g., 0.2 mole), and sodium chloride (6.5 g., 0.11 mole) in 120 ml. of dimethyl sulfoxide is heated at 130°–150° C. for 6 hours until evolution of carbon dioxide is completed. The mixture is cooled, treated with 400 ml. of water and the oily product taken up in ether, washed with water and dried over sodium sulfate. Evaporation of the ether in vacuo leaves the title compound as a yellow viscous oil.

Step D. Preparation of 8-methylsulfonyl-12-hydroxy-5-heptadecynoic acid

Methyl 8-methylsulfonyl-12-acetoxy-5-heptadecynoate (41.6 g., 0.10 mole) is added to a solution of sodium hydroxide (12.0 g., 0.3 mole) in water (120 ml.) and methanol (600 ml.). The resulting solution is heated at 55°–60° C. for 24 hours. Most of the methanol is removed by evaporation in vacuo. The residue is diluted with water and extracted with ether. The aqueous solution is acidified with concentrated hydrochloric acid. The product which separates is taken up in ether, washed with water and dried over sodium sulfate.

Evaporation of the ether in vacuo leaves the title compound as a viscous yellow oil. Purification is effected by column chromatography on silica gel with 2% methanol in chloroform as eluant. The title compound is obtained as a nearly colorless viscous oil.

EXAMPLE 11

Preparation of 8-methylsulfonyl-12-hydroxy-5-cis-heptadecenoic acid

8-Methylsulfonyl-12-hydroxy-5-heptadecynoic acid (Example 10) (3.6 g., 0.01 mole) is dissolved in ethyl acetate (50 ml.). Lindlar catalyst (1.0 g.) is added and the mixture is hydrogenated at 1 atmosphere and 25° C. When 0.01 mole of hydrogen is absorbed, the catalyst is removed by filtration and the solvent evaporated in vacuo. The oil residue consisting of the crude product is purified by column chromatography on silica gel with 2% methanol in chloroform as eluant. 8-Methylsulfonyl-12-hydroxy-5-cis-heptadecenoic acid is obtained as a colorless viscous oil.

EXAMPLE 12

Preparation of 8-methylsulfonyl-12-hydroxy-10-heptadecenoic acid

Step A. Preparation of 1-bromo-4-acetoxy-2-nonene

A mixture of 4-acetoxy-2-nonene (73.5 g., 0.4 mole), N-bromosuccinimide (80.0 g., 0.45 mole), and carbon tetrachloride (500 ml.) is boiled under reflux for 3 hours. The mixture is then cooled and the suspended succinimide removed by filtration. The carbon tetrachloride solution is washed with dilute sodium bicarbonate solution and water, and is dried over sodium sulfate. The carbon tetrachloride is evaporated in vacuo and the residual oil is distilled to yield 62 g. (59%) of 1-bromo-4-acetoxy-2-nonene as a light yellow oil, b.p. 110°–112° C./0.1 mm.

Step B. Preparation of methyl 8-methoxycarbonyl-8-methyl-sulfonyl-12-acetoxy-10-heptadecenoate This compound is prepared by the procedure of Example 3, Step C, except that 1-iodo-4-acetoxy-nonane is replaced by 1-bromo-4-acetoxy-2-nonene.

Step C. Preparation of methyl 8-methylsulfonyl-12-acetoxy-10-heptadecenoate

This compound is prepared by the procedure of Example 3, Step D, except that the methyl 8-methoxycarbonyl-8-methylsulfonyl-12-acetoxyheptadecanoate is replaced by an equivalent quantity of methyl 8-methoxycarbonyl-8-methylsulfonyl-12-acetoxy-10-heptadecenoate.

Step D. Preparation of 8-methylsulfonyl-12-hydroxy-10-heptadecenoic acid

This compound is prepared by the procedure of Example 3, Step E, except that the methyl 8-methylsulfonyl-12-acetoxyheptadecanoate is replaced by an equivalent quantity of methyl 8-methylsulfonyl-12-acetoxy-10-heptadecenoate.

EXAMPLE 13

Preparation of 8-methylsulfonyl-12(S)-hydroxy-10-heptadecynoic acid

Step A-1. Preparation of 3(S)-acetoxy-1octyne (S)-1-Octyn-3-ol (100 g., 0.794 mole) is dissolved in pyridine (79 g., 1.0 mole) and acetic anhydride (81.6 g., 0.80 mole) is added dropwise with stirring during one hour. The temperature rises to 45° C. The solution is heated at 55° C. for 1 hour and is then cooled and poured into 200 ml. ice-cold 5% hydrochloric acid. The oily product is taken up in ether, washed with water and brine and dried over sodium sulfate. The ether is evaporated and the residual oil distilled to yield 106.4 g. (80%) of 3(S)-acetoxy-1-octyne, b.p. 91°–92° C./15 mm.; $[\alpha]_D^{26} -79°$ (C 3.0, CHCl$_3$).

Step A-2. Preparation of 1-diethylamino-4(S)-acetoxy-2-nonyne

A mixture of 3(S)-acetoxy-1-octyne (58.5 g., 0.35 mole), diethylamine (28.5 g., 0.39 mole), paraformaldehyde (13.8 g., 0.46 mole) and p-dioxane (60 ml.) is heated on the steam bath under a reflux condenser for 17 hours. The resulting solution is cooled and diluted with 250 ml. of ether. The solution is extracted with 300 ml. of 5% hydrochloric acid. The acidic aqueous extract is made basic with 10% sodium hydroxide solution. The liberated amine is taken up in ether, washed with water and brine and dried over sodium sulfate. The ether is evaporated and the residual oil distilled to yield 73.1 g. (89%) of 1-diethylamino-4(S)-acetoxy-2-nonyne, b.p. 103-109°/0.3 mm.; $[\alpha]_D^{26}$-80° (C 3.3, CHCl$_3$).

Step A-3. Preparation of 1-bromo-4(S)-acetoxy-2-nonyne

A solution of 1-diethylamino-4(S)-acetoxy-2-nonyne (50.6 g., 0.20 mole) and cyanogen bromide (21.2 g., 0.20 mole) in ether (250 ml.) is allowed to stand at 25°–27° C. for 18 hours. The ether solution is washed with 5% hydrochloric acid solution, water, and brine and dried over sodium sulfate. The ether is evaporated and the residual oil distilled. After a forerun of diethylcyanamide, there is collected 34.1 g. (65%) of 1-bromo-4(S)-acetoxy-2-nonyne, b.p. 97-105°/0.2 mm.; $[\alpha]_D^{26}$-83° (C 3.7, CHCl$_3$).

Step B. Preparation of methyl 8-methoxycarbonyl-8-methylsulfonyl)-12(S)-acetoxy-10-heptadecynoate The synthesis of this compound is carried out by the method of Example 3, Step C, except that 1-iodo-4-acetoxynonane is replaced by an equivalent quantity of 1-bromo-4(S)-acetoxy-2-nonyne.

Step C. Preparation of methyl 8-methylsulfonyl-12(S)-acetoxy-10-heptadecynoate

The synthesis of this compound is carried out by the method of Example 3, Step D, except that methyl 8-methoxycarbonyl-8-methylsulfonyl-12-acetoxyheptadecanoate is replaced by an equivalent quantity of methyl 8-methoxycarbonyl-8-methylsulfonyl-12(S)-acetoxy-10-heptadecynoate.

Step D. Preparation of 8-methylsulfonyl-12(S)-hydroxy-10-heptadecynoic acid

The synthesis of this compound is carried out by the method of Example 3, Step E, except that methyl 8- methylsulfonyl-12-acetoxyheptadecanoate is replaced by an equivalent quantity of methyl 8-methylsulfonyl-12(S)-acetoxy-10-heptadecynoate.

EXAMPLE 14

Preparation of 8-methylsulfonyl-12(R)-hydroxy-10-heptadecynoic acid

By following exactly the same procedures described in Example 13 but beginning with R-1-octyn-3-ol instead of S-1-octyn-3-ol, there are obtained successively: Step A-1, 3(R)-acetoxy-1-octyne $[\alpha]_D^{26}+70°$ (C 3.1, CHCl$_3$); Step A-2, 1-diethylamino-4(R)-acetoxy-2-nonyne $[\alpha]_D^{26}+74°$ (C 3.2, CHCl$_3$);

Step A-3, 1-bromo-4(R)-acetoxy-2-nonyne $[\alpha]_D^{26}+75°$ (C 3.2, CHCl$_3$);

Step B, methyl 8-methoxycarbonyl-8-methylsulfonyl-12(R)-acetoxy-10-heptadecynoate;

Step C, methyl 8-methylsulfonyl-12(R)-acetoxy-10-heptadecynoate;

Step D, 8-methylsulfonyl-12(R)-hydroxy-10-heptadecynoic acid.

EXAMPLE 15

Preparatin of 8-methylsulfonyl-12(S)-hydroxyheptadecanoic acid

8-Methylsulfonyl-12(S)-hydroxy-10-heptadecynoic acid (36.0 g., 0.10 mole) and 5% platinum-on-charcoal catalyst (4.0 g.) are placed in a mixture of ethyl acetate (100 ml.) and cyclohexane (200 ml.) and hydrogenated in a Parr apparatus with an initial hydrogen pressure of 45 pounds per square inch. The uptake of the required 0.2 mole of hydrogen is complete in 20 minutes. The catalyst is removed by filtration and the solvents evaporated to leave the product as a residual oil weighing 33.5 g. It is purified by chromatography on silica gel with benzene-dioxane-acetic acid elution. The title compound is obtained as a nearly colorless viscous oil.

EXAMPLE 16

Preparation of 8-methylsulfonyl-12(R)-hydroxyheptadecanoic acid

The synthesis of the compound is carried out by the procedure described in Example 15 except that the 8-methylsulfonyl-12(S)-hydroxy-10-heptadecynoic acid is replaced by an equivalent quantity of 8-methylsulfonyl-12(R)-hydroxy-10-heptadecynoic acid.

EXAMPLE 17

Preparation of 8-methylsulfonyl-12-hydroxy-12-methylheptadecanoic acid

Step A. Preparation of 8-methylsulfonyl-12-oxoheptadecanoic acid

A solution of 8-methylsulfonyl-12-hydroxyheptadecanoic acid (Example 2) (10.9 g., 0.03 mole) in acetone (30 ml.) is cooled to 5°–10° C. and treated dropwise over 2-¼ hours with a solution of chromium trioxide (2.6 g., 0.026 mole) in water (7.5 ml.) and concentrated sulfuric acid (2.1 ml.). Stirring is continued for an additional thirty minutes.

The reaction mixture is then diluted with 240 ml. of water. The oil which separates is taken up in ether, washed with water and dried over sodium sulfate. The ether is evaporated in vacuo to leave the title compound in quantitative yield as a yellow viscous oil. It is used in Step B without further purification.

Step B. Preparation of 8-methylsulfonyl-12-hydroxy-12-methylheptadecanoic acid A solution of methylmagnesium bromide in tetrahydrofuran is prepared by passing gaseous methyl bromide into a stirred suspension of magnesium (2.4 g., 0.1 mole) in tetrahydrofuran (60 ml.) until all of the magnesium is consumed. The resulting solution is cooled in a 25° C. water bath and stirred while solution of 8-methylsulfonyl-12-oxoheptadecanoic acid (10.8 g., 0.03 mole) in tetrahydrofuran (20 ml.) is added dropwise during 30 minutes. The mixture (a slurry) is heated a reflux for 45 minutes, then cooled and poured into 200 ml. of a cold saturated aqueous ammonium chloride solution. The product is extracted into ether, washed with water and dried over sodium sulfate. The ether is evaporated and the crude product purified by chromatography on silica gel with 3% methanol in chloroform as eluant. 8-Methylsulfonyl-12-hydroxy-12-methylheptadecanoic acid is obtained as a very viscous colorless oil.

EXAMPLE 18

Preparation of 8-methylsulfonyl-12-hydroxy-13,13-dimethylheptadecanoic acid

Step A-1. Preparation of 4,4-dimethyl-1-octyn-3-ol

Lithium acetylide ethylene diamine complex (23 g., 0.25 mole) is suspended in a mixture of tetrahydrofuran (50 ml.) and benzene (50 ml.), and 2,2-dimethylhexanal (28.5 g., 0.224 mole) is added dropwise during 30 minutes with good stirring. The mixture is stirred and heated at 45°–50° C. for 2 hours and at 25° C. for 18 hours. Water (50 ml.) is then added during 30 minutes and the mixture is heated at reflux for one hour. It is then cooled and treated with ether (100 ml.) and water (100 ml.). The organic layer is separated, washed with water, and dried over sodium sulfate. The solvents are evaporated and the residual oil distilled in vacuo to obtain 17.7 g. (51%) of 4,4-dimethyl-1-octyn-3-ol, a colorless oil, b.p. 96°–100° C. at 18 mm. Hg.

Step A-2. Preparation of 3-acetoxy-4,4-dimethyl-1-octyne

A solution of 4,4-dimethyl-1-octyne-3-ol (17.70 g., 0.115 mole) in pyridine (11.39 g., 0.144 mole) is treated, dropwise, over 1 hour with acetic anhydride (12.95 g., 0.127 mole). The clear, colorless solution is heated at 60° C. for 5 hours.

The cooled reaction solution is poured into ice-cold 5% hydrochloric acid (25 ml.) and the resulting oil is extracted with ether. The combined extracts are washed with water, then brine and dried over anhydrous sodium sulfate. The solvent is removed under vacuum and the residual oil is distilled to give the title compound as a colorless oil, yield 16.37 g. (73%), b.p. 98-99° C./14 mm.

Anal. calcd. for $C_{12}H_{20}O_2$: C, 73.43; H, 10.27. Found: C, 73.89; H, 10.34

Step A-3. 1-Diethylamino-4-acetoxy-5,5-dimethyl-2-nonyne

A mixture of 3-acetoxy-4,4-dimethyl-1-octyne (16.20 g., 0.0826 mole), diethylamine (6.65 g., 0.0909 mole), paraformaldehyde (3.22 g., 0.1074 mole) and dioxane (15 ml.) is heated on a stem bath for 3 hours.

The cooled-in-ice reaction mixture is treated with ether (50 ml.) and the product is extracted into ice-cold H$_2$O (57.5 ml.) containing concentrated hydrochloric acid (11.5 ml.). The cold aqueous, acidic solution is basified with ice-sold water (57.5 ml.) containing sodium ydroxide (7 g.). The oily amine is extracted with ether; the combined extracts are washed with water and dried over anhydrous sodium sulfate. The solvent is removed under vacuum and the residual oil is distilled to give the title compound as a colorless oil, yield 10.65 g. (46%), b.p. 161°–162° C./14 mm.

Anal. calcd. for C$_{17}$H$_{31}$NO$_2$: C, 72.55; H, 11.10; N, 4.98. Found: C, 72.00; H, 11.05; N, 5.02.

Step A-4. Preparation of 1-bromo-4-acetoxy-5,5-dimethyl-2-nonyne

A solution of cyanogen bromide (36.0 g., 0.340 mole) in ether (400 ml.) is treated with 1-diethylamino-4-acetoxy-5,5-dimethyl-2-nonyne (82.3 g., 0.293 mole) to give a mildly exothermic reaction. The clear solution is allowed to stand at room temperature for 16 hours.

The reaction solution is washed successively with cold 5% hydrochloric acid, water, brine and the dried over anhydrous sodium sulfate. The solvent is removed under vacuum and the residual oil is distilled to give the title compound as a colorless oil, yield 60.6 g. (72%), b.p. 115-117° C./0.4 mm.

Anal. calcd. for C$_{13}$H$_{21}$BrO$_2$: C, 53.99; H, 7.32. Found: C, 54.10; H, 7.36.

Step B. Preparation of methyl 8-methoxycarbonyl-8-methylsulfonyl-12-acetoxy-13,13-dimethyl-10-heptadecynoate The synthesis of this compound is carried out by the procedure of Example 3, Step C, except that 1-iodo-4-acetoxynonane is replaced by an equivalent quantity of 1-bromo-4-acetoxy-5,5-dimethyl-2-nonyne.

Step C. Methyl 8-methylsulfonyl-12-acetoxy-13,13-dimethyl-10-heptadecynoate

The synthesis of this compound is carried out by the procedure of Example 3, Step D, except that methyl 8-methoxycarbonyl-8-methylsulfonyl-12-acetoxyheptadecanoate is replaced by an equivalent quantity of methyl 8-methyoxycarbonyl-8-methylsulfonyl-12-acetoxy-13,13-dimethyl-10-heptadecynoate.

Step D. 8-Methylsulfonyl-12-hydroxy-13,13-dimethyl-10-heptadecynoic acid

The synthesis of this compound is carried out by the procedure of Example 3, Step E, except that methyl 8-methylsulfonyl-12-acetoxyheptadecanoate is replaced by an equivalent amount of methyl 8-methylsulfonyl-12-acetoxy-13,13-dimethyl-10-heptadecynoate.

Step E. 8-Methylsulfonyl-12-hydroxy-13,13-dimethylheptadecanoic acid

The synthesis of this compound is carried out by hydrogenation exactly as described in Example 15 except that 8-methylsulfonyl-12(S)-hydroxy-10-heptadecynoic acid is replaced by an equivalent quantity of 8-methylsulfonyl-12-hydroxy-13,13-dimethyl-10-heptadecynoic acid.

EXAMPLE 19

Preparation of 8-methylsulfonyl-11-(1-hydroxycyclohexyl)-10-undecynoic acid

Step A-1. Preparation of 1-acetoxy-1-ethynylcyclohexane

1-Ethynylcyclohexan-1-ol(100 g., 0.8 mole) is added dropwise with stirring to a mixture of acetic anhydride (86.7 g., 0.85 mole) and sulfuric acid (0.25 ml.). The temperature of the reaction mixture is kept at 10°–12° C. during the addition by means of an ice bath. The mixture is then stirred without cooling for 1.5 hours. It is then poured into 300 ml. of ice water. The oily product is taken up in ether, washed with water, dilute sodium bicarbonate solution and brine and dried over sodium sulfate. Distillation affords 107 g. (80%) of 1-acetoxy-1-ethynylcyclohexane, b.p. 95°–97° C. 15 mm.

Step A-2. Preparation of 1-acetoxy-1-(3-diethylamino-1-propynyl)-cyclohexane A mixture of 1-acetoxy-1-ethynylcyclohexane (64.00 g., 0.385 mole), diethylamine (30.95 g., 0.424 mole), paraformaldehyde (15.00 g., 0.500 mole), cuprous chloride (1.5 g.) and dioxane (60 ml.) is stirred well. An exothermic reaction gradually results which may require external cooling to prevent spillage. After this initial reaction, the mixture is heated on a steam bath for 1.5 hours.

The cooled reaction mixture is treated with ether and the product is extracted into ice-cold 5% concentrated hydrochloric acid. This cold aqueous acidic solution is then basified with ice-cold 10% sodium hydroxide. The oily amine is extracted with ether and the combined extracts are washed with saturated sodium chloride solution and then dried over anhydrous sodium sulfate. The solvent is removed under vacuum and the residual oil is distilled to give 72.7 g. (75%) of light yellow oil, b.p. 113°–115° C./0.15 mm.; pmr (CDCl$_3$) S 1.07 (6H, t), 2.02 (3H, s CH$_3$COO), 2.60 (4H, q CH$_3$C$\underline{H}_2$N), 3.52 (2H, s CH$_2$C≡).

Step A-3. Preparation of 1-acetoxy-1-(3-bromo-1-propynyl)-cyclohexane

Cyanogen bromide (31.8 g., 0.3 mole) is added to a solution of 1-acetoxy-1-(3-diethylamino-1-propynyl)-cyclohexane (61 g., 0.24 mole) and the resulting solution is allowed to stand at 25°–27° C. for 18 hours. The ether solution is washed with 5% hydrochloric acid solution, water and brine and dried over sodium sulfate. The ether is evaporated and the residual oil distilled. There is obtained 34.8 g. (55%) of 1-acetoxy-1-(3-bromo-1-propynyl)-cyclohexane, a slightly yellowish oil, b.p. 114°–120° C./0.2mm.

Step B. Methyl 8-methoxycarbonyl-8-methylsulfonyl-11-(1-acetoxycyclohexyl)-10-undecynoate The synthesis of this compound is carried out by the procedure of Example 3, Step C, except that 1-iodo-4-acetoxynonane is replaced by an equivalent quantity of 1-acetoxy-1-(3-bromo-1-propynyl)-cyclohexane.

Step C. Preparation of methyl 8-methylsulfonyl-11-(1-acetoxycyclohexyl)-10-undecynoate The synthesis of this compound is carried out by the procedure of Example 3, Step D, except that methyl 8-methoxycarbonyl-8-methylsulfonyl-12-acetoxyheptadecanoate is replaced by an equivalent quantity of methyl 8-methoxycarbonyl-8-methylsulfonyl-11-(1-acetoxycyclohexyl)-10-undecynoate.

Step D. Preparation of 8-methylsulfonyl-11-(1-hydroxycyclohexyl)-10-undecynoic acid The synthesis of this compound is carried out by the procedure of Example 3, Step E, except that methyl 8-methylsulfonyl-12-acetoxyheptadecanoate is replaced by an equivalent quantity of methyl 8-methylsulfonyl-11-(1-acetoxycyclohexyl)-10-undecynoate.

EXAMPLE 20

Preparation of 8-methylsulfonyl-11-(1-hydroxycyclohexyl)-undecanoic acid

The synthesis of this compound is carried out by the hydrogenation process described in Example 15 except that 8-methylsulfonyl-12(S)-hydroxy-10-heptadecynoic acid is replaced by an equivalent quantity of 8-methylsulfonyl-11-(1-hydroxycyclohexyl)-10-undecynoic acid (Example 19).

EXAMPLE 21

Preparation of 8-methylsulfonyl-12-hydroxy-16-heptadecenoic acid

Step A. Preparation of 1-chloro-4-acetoxy-8-nonene

The synthesis of this compound is carried out by the procedures of Example 1, Steps B-1 to B-3 except that the amyl bromide of Step B-1 is replaced by an equivalent quantity of 5-bromo-1-pentene. There are obtained in order:

1-chloro-8-nonen-4-one (Step B-1);
1-chloro-8-nonen-4-ol (Step B-2); and
1-chloro-4-acetoxy-8-nonene (Step B-3).

Step B. Preparation of 1-iodo-4-acetoxy-8-nonene

The synthesis of this compound is carried out as in Example 3, Step B2, except that 1-chloro-4-acetoxynonane is replaced by an equivalent quantity of 1-chloro-4-acetoxy-8-nonene.

Step C. Preparation of methyl 8-methoxycarbonyl-8-methylsulfonyl-12-acetoxy-16-heptadecenoate The synthesis of this compound is carried out as in Example 3, Step C except that the 1-iodo-4-acetoxynonane is replaced by an equivalent quantity of 1-iodo-4-acetoxy-8-nonene.

Step D. Preparation of methyl 8-methylsulfonyl-12-acetoxy-16-heptadecenoate The synthesis of this compound is carried out as in Example 3, Step D, except that the methyl 8-methoxycarbonyl-8-methylsulfonyl-12-acetoxyheptadecanoate is replaced by an equivalent quantity of methyl 8-methoxycarbonyl-8-methylsulfonyl-12-acetoxy-16-heptadecenoate.

Step E. Preparation of 8-methylsulfonyl-12-hydroxy-16-heptadecenoic acid

The synthesis of this compound is carried out as in Example 3, Step E, except that the methyl 8-methylsulfonyl-12-acetoxyheptadecenoate is replaced by an equivalent quantity of 8-methylsulfonyl-12-acetoxy-16-heptadecenoate.

EXAMPLE 22

Preparation of 8-methylsulfonyl-12-hydroxy-17, 17, 17trifluoroheptadecanoic acid The synthesis of this compound is carried out by the procedures of Example 1 for the initial steps and the procedure of Example 2 for the final step, except that in step B-1 of Example 1 an equivalent amount of 1,1,1-trifluoro-5-bromopentane is substituted for amyl bromide. Thus, there are obtained in order: di-tert-butyl-(6-ethoxycarbonylhexyl)-malonate (Step A); 1-chloro-9,9,9-trifluoro-4-nonanone (Step B-1); 1-chloro-9,9,9-trifluoro-4-nonanol (Step B-2); 1-chloro-9,9,9-trifluoro-4-acetoxynonane (Step B-3); di-tert.-butyl-2-(4-acetoxy-9,9,9-trifluorononyl)-2-(6-ethoxycarbonylhexyl)-malonate (Step C); ethyl 8-carboxy-12-acetoxy-17,17,17-trifluoroheptadecanoate (Step D); ethyl 8-bromo-12-acetoxy-17,17,17-trifluoroheptadecanoate (Step E); 8-methylthio-12-hydroxy-17,17,17-trifluoroheptadecanoic acid (Step F); and 8-methylsulfonyl-12-hydroxy-17,17,17-trifluoroheptadecanoic acid (prepared as in Example 2 as explained above).

EXAMPLE 23

Preparation of 8-methylsulfonyl-12-hydroxy-16,16-dimethylheptadecanoic acid

The synthesis of this compound is carried out by the procedures of Example 1 for the initial steps and the procedure of Example 2 for the final step, except that in Step B-1 of Example 1 an equivalent amount of 1-bromo-4,4-dimethylpentane is substituted for amyl bromide. Thus, there are obtained in order:

di-tert.-butyl (6-ethoxycarbonylhexyl)-malonate (Step A);
1-chloro-8,8-dimethyl-4-nonanone (Step B-1);
1-chloro-8,8-dimethyl-4-nonanol (Step B-2);
1-chloro-8,8-dimethyl-4-acetoxynonane (Step B-3);
di-tert.-butyl 2-(4-acetoxy-8,8-dimethylnonyl)-2-(6-ethoxycarbonylhexyl)-malonate (Step C);
ethyl 8-carboxy-12-acetoxy-16,16-dimethylheptadecanoate (Step D);
ethyl 8-bromo-12-acetoxy-16,16-dimethylheptadecanoate (Step E);
8-methylthio-12-hydroxy-16,16-dimethylheptadecanoic acid (Step F); and
8-methylsulfonyl-12-hydroxy-16,16-dimethylheptadecanoic acid (prepared as in Example 2 as explained above).

EXAMPLE 24

Preparation of 8-methylsulfonyl-12-hydroxy-13-(4-fluorophenoxy)-tridecanoic acid

Step A-1. Preparation of 4-fluorophenoxyacetaldehyde diethylacetal

A solution of p-fluorophenol (28.1 g., 0.25 mole) in dimethylformamide (30 ml.) is added dropwise to a suspension of hexane (2 × 30 ml.)-prewashed sodium hydride (50% oil dispersion, 12.5 g., 0.26 mole) in dimethyl-formamide (120 ml.). The resulting mixture is stirred at room temperature for 10 minutes, treated with bromoacetaldehyde diethylacetal (49.3 g., 0.25 mole), and finally heated on a steam bath for 4 hours. The reaction mixture is allowed to come to room temperature and the precipitated sodium bromide is filtered off. Dimethylformamide is then removed on a rotary evaporator, the oil residue is diluted with acetone (100 ml.) and another quantity of sodium bromide is precipitated which again is removed by filtration. The filtrate is then concentrated on a rotary evaporator leaving an oil residue which is vacuum distilled at 87° C./0.05 mm. to yield the desired product as colorless oil (46.7 g., 0.205 mole, 82%). ir (neat) 3.4~3.5, 6.21, 6.64, 8.00, 8.25, 8.83, 9.32, 12.08, 13.20μ; pmr (CCl$_4$)δ1.17 (6H, t, J=7.5Hz), 3.57 (2H, q, J=7.5Hz), 3.61 (2H, q, J=7.5Hz), 3.85 (2H, d, J=5Hz), 4.68 (1H, t, J=5Hz), 6.6–7.1 (4H, m).

Step A-2. Preparation of 4-fluorophenoxyacetaldehyde

A mixture of 4-fluorophenoxyacetaldehyde (30.0 g., 0.131 mole), acetone (150 ml.), water (150 ml.) and concentrated sulfuric acid (0.8 ml.) is refluxed overnight (ca. 16 hours). The mixture is allowed to cool to room temperature, and is then extracted with methylenechloride four times. The combined extracts are washed with aqueous sodium bicarbonate and dried over anhydrous magnesium sulfate. The solvent is stripped off on a rotary evaporator and the oil residue is subsequently distilled in vacuo at 70° C./0.05 mm. to give the title compound (19.0 g., 0.123 mole, 94%). ir (neat) 3.23, 3.50, 3.63, 5.71, 6.62, 7.00, 8.00, 8.24, 9.07, 9.38, 12.03, 12.51, 13.12μ; pmr (CCl$_4$)δ4.37 (2H, d, J=1Hz), 6.6–7.1 (4H, m), 9.68 (1H, t, J=1Hz).

Step A-3. Preparation of 5-(4-fluorophenoxy)-1-penten-4-ol

To a mixture of ether (50 ml.) and magnesium turnings (4.49 g., 0.185 mole) is added a small amount of allyl bromide (ca. 0.5 g.). The mixture is stirred until Grignard reagent is formed (reflux of ether is a good sign). A solution of allyl bromide (24.2 g., 0.20 mole) and 4-fluorophenoxyacetaldehyde (19.0 g., 0.123 mole) in ether (110 ml.) is then added at such a rate as to maintain the reflux of ether. The resulting mixture is heated at reflux for another hour, cooled in an ice bath, and treated with dilute sulfuric acid (1.6 M, 70 ml.). The organic phase is separated and the aqueous phase is extracted with ether three times. The combined extracts are washed with 5% sodium bicarbonate, dried over anhydrous magnesium sulfate and finally concentrated on a rotary evaporator. The oil residue is vacuum distilled at 73° C./0.03 mm. to afford the desired product (18.6 g., 0.095 mole, 77%). ir (neat) 2.90, 3.22, 3.40, 6.05, 6.20, 6.62, 8.00, 8.25, 10.87, 12.10, 13.14μ; pmr (CCl$_4$)δ2.32 (2H, t, J=6Hz), 2.54 (1H, m), 3.6–4.1 (3H, m), 4.8–5.05(1H, m), 5.05–5.25 (1H, m), 5.4–6.3 (1H, m), 6.6–7.1 (4H, m).

Step A-4. Preparation of 4-benzyloxy-5-(4-fluorophenoxy)-1-pentene

A solution of 5-(4-fluorophenoxy)-1-penten-4-ol (9.81 g., 50 mmoles) in dimethylformamide (15 ml.) is added dropwise to a suspension of hexane (2 × 10 ml.) prewashed sodium hydride (50% oil dispersion, 2.64 g., 55mmoles) in dimethylformamide (45 ml.). The resulting mixture is stirred until gas evolution ceases. (A few drops of methanol may be needed to initiate the evolution of hydrogen). The reaction mixture is chilled in an ice bath and treated with a solution of benzyl bromide (10.30 g., 60 mmoles) in dimethylformamide (10 ml.). The reaction mixture is then stirred at room temperature overnight (ca. 16 hours), and then heated on a steam bath for 1 hour. The reaction mixture is diluted with cold water (50 ml.), and extracted with ether four times. The combined extracts are washed with 2N hydrochloric acid and saturated brine and finally dried over anhydrous magnesium sulfate. After the removal of the solvent, the oil residue is vacuum distilled at 112°~6° C./0.025 mm. to give the title compound (13.1 g., 45.7 mmoles, 92%). ir (neat) 3.3~3.5, 6.08, 6.21, 6.65, 8.01, 8.28, 9.13, 10.90, 12.10, 13.18, 13.60, 14.40μ; pmr (CCl$_4$)δ2.37 (2H, t, J-5Hz), 3.5–4.0 (3H, m), 4.57 (2H, s), 4.8–5.05 (1H, m), 5.05–5.25 (1H, m), 5.4–6.2 (1H, m), 6.6–7.1 (4H, m), 7.19 (5H, s).

Anal. calcd. for C$_{18}$H$_{19}$FO$_2$: C, 75.50; H, 6.69
Found: C, 75.10; H, 6.70

Step A-5. Preparation of 4-benzyloxy-5-(4-fluorophenoxy)-1-pentanol

To a mixture of 4-benzyloxy-5-(4-fluorophenoxy)-1-pentene (2.86 g., 10 mmoles), sodium borohydride (0.47 g., 12.5 mmoles), and tetrahydrofuran (25 ml.) is added dropwise a solution of boron fluoride etherate (2.1 ml., 16.7 mmoles) in tetrahydrofuran (5 ml.) at ice-bath temperatures under a nitrogen atmosphere. The resulting mixture is further stirred at room temperature overnight (ca.15 hours). The reaction flask is chilled in an ice bath and water (2 ml.) is very cautiously added to destroy the excess hydride, followed by the additions of sodium hydroxide (5N, 4 ml.) and hydrogen peroxide (30%, 8 ml.). The final mixture is stirred at room temperature for one-half hour, diluted with cold water and then extracted with chloroform three times. The combined extracts are washed with saturated brine and dried over anhydrous magnesium sulfate. The solvent is evaporated in vacuo leaving the title compound as a viscous oil (3.00 g., 10 mmoles, 100%). ir (neat) 2.97, 3.30, 3.41, 6.22, 6.68, 6.90, 8.03, 8.30, 9.16, 9.44, 12.10, 13.20, 13.60, 14.40μ; pmr (CCl$_4$)δ1.4–1.9 (4H, m), 3.2–4.2 (6H, m), 4.58 (2H, broad s), 6.6–7.1 (4H, m), 7.20 (5H, s).

Step A-6. Preparation of 4-benzyloxy-5-(4-fluorophenoxy)-1-pentanol tosylate

4-Benzyloxy-5-(4-fluorophenoxy)-1-pentanol (3.00 g., 10 mmoles) is added to a solution of p-toluenesulfonyl chloride (2.28 g., 12 mmoles) in pyridine (10 ml.). The resulting mixture is stirred and placed in a refrigerator overnight (ca. 16 hours).

The mixture is poured into ice water and extracted with ether three times. The combined extracts are washed with 2N hydrochloric acid until acidic and then 5% sodium bicarbonate and dried over anhydrous magnesium sulfate. The solvent is removed by evaporation leaving the title compound as viscous oil (3.78 g., 8.24 mmoles, 82.4%). ir (neat) 3.28, 3.40, 6.20, 6.63, 6.88, 7.38, 8.00, 8.27, 8.39, 8.49, 9.11, 10.38, 10.86, 12.07, 13.18, 13.60, 14.38μ; pmr (CCl$_4$)δ1.3–2.0 (4H, m), 2.35 (3H, s), 3.4–4.1 (4H, m), 4.4.–4.6 (2H, m), 6.6–7.3 (11H, m, containing a phenyl singlet at 7.18δ); 7.65 (2H, d, J=8Hz).

Step A-7. Preparation of 4-benzyloxy-5-(4-fluorophenoxy)-1-iodopentane

A solution of 4-benzyloxy-5-(4-fluorophenoxy)-1-pentanol tosylate (3.78 g., 8.24 mmoles) and sodium iodide (3.71 g., 25 mmoles) in acetone (70 ml.) is stirred at room temperature overnight (ca. 17 hours) and then heated on the steam bath for 15 minutes. The mixture is poured into cold water and extracted with ether three times. The combined extracts are washed with aqueous sodium thiosulfate and dried over anhydrous magnesium sulfate. The solvent is removed on a rotary evaporator to leave an oil residue which is further purified by chromatography on a silica gel (70 g.) column. Elution with chloroform gives the pure title compound (2.72 g., 6.57 mmoles, 79%). ir (neat) 3.28, 3.40, 6.20, 6.62, 6.87, 8.00, 8.23, 9.10, 12.07, 13.16, 13.58, 14.37μ; pmr $(CCl_4)\delta 1.4$–2.2 (4H, m), 3.08 (2H, t, J=6Hz), 3.5–4.1 (3H, m), 4.47 (1H, d, J=12 Hz), 4.69 (1H, d, J=12Hz), 6.6–7.1 (4H, m), 7.20 (5H, s).

Step B. Preparation of methyl 8-methylsulfonyl-8-methoxycarbonyl-12-benzyloxy-13-(4-fluorophenoxy)tridecanoate To a suspension of petroleum ether (2 × 3 ml.)prewashed sodium hydride (50% oil dispersion, 0.24 g., 5.0 mmoles) in dry dimethylformamide (10 ml.) is added a solution of dimethyl 2-methylsulfonylazelate (1.33 g., 4.5 mmoles) in dimethylformamide (5 ml.) under a nitrogen atmosphere. The resulting mixture is stirred at room temperature until gas evolution ceases, and is then treated with a solution of 4-benzyloxy-5-(4-fluorophenoxy)-1-iodopentane (2.07 g., 5.0 mmoles) in dimethylformamide (5 ml.). The mixture is then stirred at room temperature overnight (ca. 15 hours).

The reaction mixture is poured into cold water and extracted with chloroform three times. The combined extracts are washed with 2N hydrochloric acid until acidic and then washed with 5% sodium bicarbonate and finally dried over anhydrous magnesium sulfate. The solvent is evaporated in vacuo to leave the title compound (2.62 g., 4.5 mmoles, 100%) as a pale yellow viscous oil. ir (neat) 3.4, 5.76, 6.21, 6.66, 6.88, 7.66, 8.01, 8.28, 8.84, 10.41, 12.06, 13.2μ13.6, 14.37δ; pmr $(CCl_4)\delta 1.1$–2.4 (18H, m), 2.83 (3H, s), 3.4–4.1 (9H, m, containing two methyl singlets at 3.55 and 3.71δ), 6.47 (1H, d, J=12Hz), 6.70 (1H, d, J=12Hz), 6.6–7.1 (4H, m), 7.20 (5H, s).

Step C. Preparation of methyl 8-methylsulfonyl-12-benzyloxy-13-(4-fluorophenoxy)-tridecanoate A mixture of methyl 8-methylsulfonyl-8-methoxycarbonyl-12-benzyloxy-13-(4-fluorophenoxy)tridecanoate (2.60 g., 4.5 mmoles), sodium chloride (0.5 g., 8.5 mmoles), dimethylformamide (8 ml.) and water (0.2 ml.) is heated with an oil bath at 160° C overnight (ca. 15 hours). The reaction mixture is allowed to cool to room temperature, quenched with cold water, and then extracted with chloroform three times. The combined extracts are washed with brine and dried over anhydrous magnesium sulfate. The solvent is removed by evaporation in vacuo leaving the desired product as a viscous oil residue (2.30 g., 4.4 mmoles, 98%). ir (neat) 3.40, 5.72, 6.20, 6.62, 6.87, 7.71, 8.00, 8.28, 8.90, 12.04, 13.17, 14.37μ; pmr $CCl_4 \delta 1.0$–2.9 (22H, m, containing a methyl singlet at 260δ), 3.54 (3H, s); 3.5–4.1 (3H, m), 4.47 (1H, d, J=12Hz), 4.70 (1H, d, J=12Hz), 6.6–7.1 (4H, m), 7.20 (5H, s).

Step D. Preparation of 8-methylsulfonyl-12-benzyloxy-13-(4-fluorophenoxy)-tridecanoic acid Sodium hydroxide solution (1.2 ml., 5N) is added to a mixture of methyl 8-methylsulfonyl-12-benzyloxy-13-(4-fluorophenoxy)tridecanoate (2.30 g., 4.4 mmoles) in aqueous methanol (50%, 20 ml.). A mild exothermic reaction is observed during the addition and the resulting mixture is stirred at room temperature overnight (ca. 16 hours).

After the removal of the solvents on a rotary evaporator, the residue is taken up in water (ca. 30 ml.), and the solution acidified and extracted with ether three times. The combined extracts are washed with brine and then dried over anhydrous magnesium sulfate. The solvent is evaporated in vacuo leaving an oil residue which is further purified by column chromatography on silica gel (100 g.). Elution with chloroform-methanol (50:1) gives the title compound as a colorless oil (1.403 g., 2.76 mmoles, 61%). ir (neat) 2.8μ4.0, 5.85, 6.20, 6.67, 6.88, 7.76, 8.01, 8.29, 8.95, 10.46, 12.05, 13.20, 14.37μ; pmr $(CDCl_3)\delta 1.1$–3.0 (22H, m, containing a methyl singlet at 2.75δ), 3.5–4.1 (3H, m), 4.53 (1H, d, J=12Hz), 4.77 (1H, d, J=12Hz), 6.6–7.2 (4H, m), 7.27 (5H, s), 10.68 (1H, broad s).

Step E. Preparation of 8-methylsulfonyl-12-hydroxy-13-(4-fluorophenoxy)-tridecanoic acid The hydrogenolysis of 8-methylsulfonyl-12-benzyloxy-13-(4-fluorophenoxy)tridecanoic acid (1.237 g., 2.43 mmoles) in absolute ethanol (100 ml.) in the presence of 10% palladium on charcoal (0.2 g.) is carried out at 25° C. in an atmospheric-pressure hydrogenator. After hydrogen uptake stops, the catalyst is filtered off and the solvent is evaporated in vacuo to leave the title compound as a colorless oil (0.927 g., 2.21 mmoles, 91%). ir (neat) 2.8~4.0, 5.81, 6.22, 6.65, 6.86, 7.80, 8.30, 8.95, 10.46, 12.04, 13.18μ; pmr $(CDCl_3)\delta 1.1$–3.0 (22H, m, containing a methyl singlet at 2.82δ), 3.6–4.2 (3H, m), 6.2–6.7 (2H, m), 6.7–7.2 (4H, m).

Anal. calcd. for $C_{20}H_{31}FO_6S$: C, 57.40; H, 7.47 Found: C, 57.17; H, 7.32

EXAMPLE 25

Preparation of 8-methylsulfonyl-12-hydroxy-13-(4-methylphenoxy)-tridecanoic acid The synthesis of this compound is carried out by the procedures of Example 24 except that in Step A-1 of Example 24 the 4-fluorophenol is replaced by an equivalent quantity of p-cresol. Thus there are obtained in order:

4-methylphenoxyacetaldehyde diethyl acetal (Step A-1);
4-methylphenoxyacetaldehyde (Step A-2);
5-(4-methylphenoxy)-1-penten-4-ol (Step A-3);
4-benzyloxy-5-(4-methylphenoxy)-1-pentene (Step A-4);
4-benzyloxy-5-(4-methylphenoxy)-1-pentanol (Step A-5);
4-benzyloxy-5-(4-methylphenoxy)-1-pentanol tosylate (Step A-6);

4-benzyloxy-5-(4-methylphenoxy)-1-iodopentane (Step A-7);
methyl 8-methylsulfonyl-8-methoxycarbonyl-12-benzyloxy-13-(4-methylphenoxy)tridecanoate (Step B);
methyl 8-methylsulfonyl-12-benzyloxy-13-(4-methylphenoxy)tridecanoate (Step C);
8-methylsulfonyl-12-benzyloxy-13-(4-methylphenoxy)-tridecanoic acid (Step D);
8-methylsulfonyl-12-hydroxy-13-(4-methylphenoxy)-tridecanoic acid (Step E)

EXAMPLE 26

Preparation of 8-methylsulfonyl-12-hydroxy-13-(3-trifluoromethylphenoxy)tridecanoic Acid Step A-1. Preparation of 3-Trifluoromethylphenoxyacetaldehyde Diethyl Acetal A suspension of sodium hydride (57% in mineral oil) (15.52 g. net wt.; 0.648 mole) in dimethylformamide (460 ml.) is treated, dropwise, over 30 minutes with 3-trifluoromethylphenol (100.00 g.; 0.617 mole). Stirring is continued for an additional 15 minutes. The bromoacetaldehyde diethyl acetal (121.60 g.; 0.617 mole) is added, dropwise, over 15 minutes. The mixture is heated to 100° and maintained at 100° for 4 hours.

The cooled reaction mixture is treated with water (920 ml.), and the organic layer is separated. The aqueous layer is extracted with ether. The combined organic solutions are washed with saturated sodium chloride solution and then dried over anhydrous magnesium sulfate. The solvent is removed under vacuum and the residual oil is distilled to give the title compound as a colorless oil, yield 146.4 g. (85%), b.p. 100°–103°/0.2 mm.

Step A-2. Preparation of 3-Trifluoromethylphenoxyacetaldehyde

A mixture of 3-trifluoromethylphenoxyacetaldehyde diethyl acetal (146.3 g.; 0.527 mole), acetone (600 ml.), water (550 ml.), and concentrated sulfuric acid (3.5 ml.) is heated under reflux for 22 hours.

The cooled reaction mixture is extracted (four times) with methylene chloride. The combined extracts are washed with aqueous sodium bicarbonate and then dried over anhydrous magnesium sulfate. The solvent is removed under vacuum and the residual oil is distilled to give the title compound as a colorless oil, yield 85.2 g. (80%), b.p. 78°–80°/0.2 mm.

Step A-3. Preparation of 1-(2-Tetrahydropyranyloxy)-4-acetoxy-5-(3-trifluoromethylphenoxy)-2-pentyne To the Grignard reagent prepared from magnesium (12.14 g.; 0.499 mole) and bromoethane (54.38 g.; 0.499 mole) in tetrahydrofuran (350 ml.) is added, dropwise, during 30 minutes, a solution of tetrahydro-2-(2-propynyloxy-2H-pyran (67.01 g.; 0.478 mole) in tetrahydrofuran (40 ml.). The mixture is stirred at room temperature, under nitrogen for 1 hour, then treated, dropwise, during 30 minutes, with a solution of 3-trifluoromethylphenoxyacetaldehyde (85.00 g.; 0.416 mole) in tetrahydrofuran (60 ml.). The mixture is heated on a steam bath, under nitrogen for 1 hour, then chilled in an ice bath and treated, dropwise, during 30 minutes, with a mixture of acetic anhydride (50.94 g.; 0.499 mole) and pyridine (78.94 g.; 0.998 mole). The mixture is heated on a steam bath under nitrogen for 30 minutes.

The cooled mixture is poured into cold water (1200 ml.) and the organic layer is separated. The aqueous layer is extracted with ether. The combined organic extracts are washed with water and then dried over anhydrous magnesium sulfate. The solvent is removed under vacuum to give the title compound as an orange-red residual oil, yield 160.73 g.; pmr (CDCl$_3$) δ 2.10 (3H, s CH$_3$COO), 4.22 (2H, d CH$_2$O), 4.35 (2H, d CH$_2$C≡C), 5.82 (1H, m CHOCO), 7.20 (4H, m Aryl H).

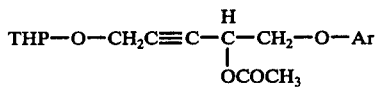

Step A-4. Preparation of 1-(2-Tetrahydropyranyloxy)-4-acetoxy-5-(3-trifluoromethylphenoxy)pentane 1-(2-Tetrahydropyranyloxy)-4-acetoxy-5-(3-trifluoromethylphenoxy)-2-pentyne (40.18 g.; 0.104 mole) is dissolved in ethyl acetate (200 ml.). 5% Palladium on carbon (5 g.) is added and the mixture is hydrogenated on the Parr apparatus at an initial pressure of 45 lbs./in$^2$ and 25°. When 0.208 mole of hydrogen is absorbed, the catalyst is removed by filtration and the solvent is evaporated under vacuum to give the title compound as a light orange residual oil, yield 40.60 g.; pmr (CDCl$_3$) δ 2.13 (3H, s CH$_3$COO), 4.10 (2H, d CH$_2$O), 5.20 (1H, m CHOCO), 7.22 (4H, m Aryl H).

Step A-5. Preparation of 4-Acetoxy-5-(3-trifluoromethylphenoxy)-1-pentanol

A mixture of 1-(2-tetrahydropyranyloxy)-4-acetoxy-5-(3-trifluoromethylphenoxy)pentane (162.4 g.; 0.416 mole), methanol (700 ml.), concentrated hydrochloric acid (3 ml.), and ethyl acetate (70 ml.) is stirred at room temperature for 1 hour.

The reaction mixture is poured into cold water (1500 ml.) and the organic layer is extracted with ether. The combined extracts are washed with saturated sodium bicarbonate solution, then brine and dried over anhydrous magnesium sulfate. The solvent is removed under vacuum and the residual oil is distilled to give the title compound as a colorless oil, yield 90.9 g. (71%), b.p. 142°–144°/0.075 mm.; pmr (CDCl$_3$) δ 2.10 (3H, s CH$_3$COO), 3.62 (2H, t HOC$\underline{H}_2$), 4.12 (2H, d CH$_2$O), 5.23 (1H, m CHOCO), 7.20 (4H, m Aryl H).

Anal. Calc'd for C$_{14}$H$_{17}$F$_3$O$_4$: C, 54.90; H, 5.59 Found: C, 54.63; H, 5.86

Step A-6. Preparation of 1-(p-Toluenesulfonyloxy)-4-acetoxy-5-(3-trifluoromethylphenoxy)pentane A solution of p-toluenesulfonyl chloride (65.2 g., 0.342 mole) in pyridine (130 ml.) is cooled in a cold water (10°–15°) bath while 4-acetoxy-5-(3-trifluoromethylphenoxy)-1-pentanol (90.7 g., 0.297 mole) is added dropwise with stirring during 70 minutes. The mixture is then stirred 2 hours in the same cold water bath. It is poured into 400 ml. of water. The oily product is taken up in ether, washed with water, 2N hydrochloric acid and dilute sodium bicarbonate solution and dried over magnesium sulfate. The solvent is evaporated in vacuo to leave 125 g. (94%) of the crude title compound as a nearly colorless oil.

Step A-7. Preparation of 1-iodo-4-acetoxy-5-(3-trifluoromethylphenoxy)pentane A solution of 1-(p-toluenesulfonyloxy)-4-acetoxy-5-(3-trifluoromethylphenoxy)pentane (125 g., 0.28 mole) and sodium iodide (126 g., 0.84 mole) in acetone (600 ml.) is allowed to stand at 25°-27° for 16 hours. The precipitated sodium tosylate is filtered off. Most of the acetone is evaporated from the filtrate and the residue is treated with 300 ml. of water. The oily product is taken up in ether, washed with dilute sodium thiosulfate solution, water, and brine, and dried over magnesium sulfate. The solvent is distilled in vacuo to yield 113 g. (97%) of the crude title compound as a yellowish oil which is used without further purification; pmr (CDCl$_3$) 2.06 (3H, s CH$_3$O); 3.20 (2H, t CH$_2$I); 4.01 (2H, d CH$_2$O); 5.20 (1H, m CHO).

Step B. Preparation of Methyl 8-methylsulfonyl-8-methoxycarbonyl-12-acetoxy-13-(3-trifluoromethylphenoxy)tridecanoate A 50% oil dispersion of sodium hydride (2.11 g., 0.044 mole) in mineral oil is washed with petroleum ether and then suspended in dry dimethylformamide (30 ml.) under a nitrogen atmosphere at room temperature. To this suspension is added a solution of dimethyl-2-methylsulfonyl-azelate (11.8 g., 0.04 mole) in dry dimethylformamide (30 ml.). After the evolution of hydrogen is completed, the mixture is cooled to 5° C. in an ice bath and a solution of 1-iodo-4-acetoxy-5-(3-trifluoromethylphenoxy)pentane (18.3 g., 0.044 mole) in dry dimethylformamide (30 ml.) is added dropwise. After 48 hours, ether is added to the reaction mixture to precipitate sodium iodide which is removed by filtration. The filtrate is concentrated in vacuo to give a residue which is diluted with water, acidified with 6N hydrochloric acid, an extracted with ether. The ether extracts are washed with water until neutral, dried over anhydrous magnesium sulfate, and concentrated in vacuo to give the title compound (20.5 g., 0.035 mole, 88%).

Step C. Preparation of Methyl 8-methylsulfonyl-12-acetoxy-13-(3-trifluoromethylphenoxy)tridecanoate A mixture of methyl 8-methylsulfonyl-8-methoxycarbonyl-12-acetoxy-13-(3-trifluoromethylphenoxy)-tridecanoate (5.82 g., 0.01 mole), sodium chloride (0.59 g., 0.01 mole), dimethylsulfoxide (8 ml.), and water (0.2 ml.) is heated in an oil bath at 185° C. for 10 hours under nitrogen. The reaction mixture is then concentrated in vacuo on a steam bath. The dark-colored residue is diluted with water, acidified with 6N hydrochloric acid, and extracted with ether. The ether extracts are washed with water, dried with anhydrous magnesium sulfate, and concentrated in vacuo to give the title compound (9.90 g., 0.019 mole, 94%).

Step D. Preparation of 8-Methylsulfonyl-12-hydroxy-13-(3-trifluoromethylphenoxy)tridecanoic acid A mixture of methyl 8-methylsulfonyl-12-acetoxy-13-(3-trifluoromethylphenoxy)tridecanoate (9.90 g., 0.019 mole), 20% aqueous sodium hydroxide (30 ml.) and methanol (30 ml.) is stirred at room temperature overnight. Then the reaction mixture is concentrated in vacuo on a steam bath. The concentrate is dissolved in water and extracted with ether. The basic aqueous solution is acidified with 6N hydrochloric acid and extracted with ether. These ether extracts are washed with water until neutral, dried over anhydrous magnesium sulfate and concentrated in vacuo to give the title compound (5.55 g., 0.0118 mole, 62%) in analytical purity.

Anal. Calc'd for C$_{21}$H$_{31}$F$_3$O$_6$S: C, 53.83; H, 6.67 Found: C, 54.02; H, 6.71

EXAMPLE 27

Preparation of 8-methylsulfonyl-12-hydroxy-13-phenoxytridecanoic acid

The synthesis of this compound is carried out by the procedures of Example 24 except that in Step A-1 of Example 24 the 4-fluorophenol is replaced by an equivalent quantity of phenol. Thus, there are obtained in order:

phenoxyacetaldehyde diethyl acetal (Step A-1);
phenoxyacetaldehyde (Step A-2);
5-phenoxy-1-penten-4-ol (Step A-3);
4-benzyloxy-5-phenoxy-1-pentene (Step A-4);
4-benzyloxy-5-phenoxy-1-pentanol (Step A-5);
4-benzyloxy-5-phenoxy-1-pentanol tosylate (Step A-6);
4-benzyloxy-5-phenoxy-1-iodopentane (Step A-7);
methyl 8-methylsulfonyl-8-methoxycarbonyl-12-benzyloxy-13-phenoxytridecanoate (Step B);
methyl 8-methylsulfonyl-12-benzyloxy-13-phenoxytridecanoate (Step C);
8-methylsulfonyl-12-benzyloxy-13-phenoxytridecanoic acid (Step D);
8-methylsulfonyl-12-hydroxy-13-phenoxytridecanoic acid (Step E).

EXAMPLE 28

Preparation of 8-methylsulfonyl-12-hydroxy-13-(2,4-dichlorophenoxy)tridecanoic acid The synthesis of this compound is carried out by the procedures of Example 24 except that in Step A-1 of Example 24 the 4-fluorophenol is replaced by an equivalent quantity of 2,4-dichlorophenol. Thus, there are obtained in order:

2,4-dichlorophenoxyacetaldehyde diethyl acetal (Step A-1);
2,4-dichlorophenoxyacetaldehyde (Step A-2);
5-(2,4-dichlorophenoxy)-1-pentan-4-ol (Step A-3);
4-benzyloxy-5-(2,4-dichlorophenoxy)-1-pentane (Step A-4);
4-benzyloxy-5-(2,4-dichlorophenoxy)-1-pentanol (Step A-5);
4-benzyloxy-5-(2,4-dichlorophenoxy)-1-pentanol tosylate (Step A-6);
4-benzyloxy-5-(2,4-dichlorophenoxy)-1-iodopentane (Step A-7);
methyl 8-methylsulfonyl-8-methoxycarbonyl-12-benzyloxy-13-(2,4-dichlorophenoxy)tridecanoate (Step B);
methyl 8-methylsulfonyl-12-benzyloxy-13-(2,4-dichloro-phenoxy)tridecanoate (Step C);
8-methylsulfonyl-12-benzyloxy-13-(2,4-dichlorophenoxy)-tridecanoic acid (Step D);
8-methylsulfonyl-12-hydroxy-13-(2,4-dichlorophenoxy)-tridecanoic acid (Step E).

EXAMPLE 29

Preparation of b 8-methylsulfonyl-12-hydroxy-13-(4-methylphenoxy)tridecanoic acid The synthesis of this compound is carried out by the procedures of Example 24 except that in Step A-1 of Example 24 the 4-fluorophenol is replaced by an equivalent quantity of 4-methoxyphenol. Thus, there are obtained in order:
4-methoxyphenoxyacetaldehyde diethyl acetal (Step A-1);
4-methoxyphenoxyacetaldehyde (Step A-2);
5-(4-methoxyphenoxy)-1-penten-4-ol (Step A-3);
4-benzyloxy-5-(4-methoxyphenoxy)-1-pentane (Step A-4);
4-benzyloxy-5-(4-methoxyphenoxy)-1-pentanol (Step A-5);
4-benzyloxy-5-(4-methoxyphenoxy)-1-pentanol tosylate (Step A-6);
4-benzyloxy-5-(4-methoxyphenoxy)-1-iodopentane (Step A-7);
methyl 8-methylsulfonyl-8-methoxycarbonyl-12-benzyloxy-13-(4-methoxyphenoxy)tridecanoate (Step B);
methyl 8-methylsulfonyl-12-benzyloxy-13-(4-methoxyphenoxy)tridecanoate (Step C);
8-methylsulfonyl-12-benzyloxy-13-(4-methoxyphenoxy)tridecanoic acid (Step D);
8-methylsulfonyl-12-hydroxy-13-(4-methoxyphenoxy)tridecanoic acid (Step E).

EXAMPLE 30

Preparation of 8-methylsulfonyl-12-hydroxy-13-(3-pyridyloxy)-tridecanoic acid

The synthesis of this compound is carried out by the procedures of Example 24 except that in Step A-1 of Example 24 the 4-fluorophenol is replaced by an equivalent quantity of 3-hydroxypyridine. Thus, there are obtained in order:
3-pyridyloxyacetaldehyde diethyl acetal (Step A-1);
3-pyridyloxyacetaldehyde (Step A-2);
5-(3-pyridyloxy)-1-penten-4-ol (Step A-3);
4-benzyloxy-5-(3-pyridyloxy)-1-pentene (Step A-4);
4-benzyloxy-5-(3-pyridyloxy)-1-pentanol (Step A-5);
4-benzyloxy-5-(3-pyridyloxy)-1-pentanol tosylate (Step A-6);
4-benzyloxy-5-(3-pyridyloxy)-1-iodopentane (Step A-7);
methyl 8-methylsulfonyl-8-methoxycarbonyl-12-benzyloxy-13-(3-pyridyloxy)-tridecanoate (Step B);
methyl 8-methylsulfonyl-12-benzyloxy-13-(3-pyridyloxy)-tridecanoate (Step C);
8-methylsulfonyl-12-benzyloxy-13-(3-pyridyloxy)-tridecanoic acid (Step D);
8-methylsulfonyl-12-hydroxy-13-(3-pyridyloxy)-tridecanoic acid (Step E).

EXAMPLE 31

Preparation of 8-methylsulfonyl-12-hydroxy-13-propoxytridecanoic acid

The synthesis of this compound is carried out by the procedures of Example 24 except that in Step A-1 of Example 24 the 4-fluorophenol is replaced by an equivalent quantity of 1-propanol. Thus, there are obtained in order:
propoxyacetaldehyde diethyl acetal (Step A-1);
propoxyacetaldehyde (Step A-2);
5-propoxy-1-penten-4-ol (Step A-3);
4-benzyloxy-5-propoxy-1-pentene (Step A-4);
4-benzyloxy-5-propoxy-1-pentanol (Step A-5);
4-benzyloxy-5-propoxy-1-pentanol tosylate (Step A-6);
4-benzyloxy-5-propoxy-1-iodopentane (Step A-7);
methyl 8-methylsulfonyl-8-methoxycarbonyl-12-benzyloxy-13-propoxytridecanoate (Step B);
methyl 8-methylsulfonyl-12-benzyloxy-13-propoxytridecanoate (Step C);
8-methylsulfonyl-12-benzyloxy-13-propoxytridecanoic acid (Step D);
8-methylsulfonyl-12-hydroxy-13-propoxytridecanoic acid (Step E).

EXAMPLE 32

Methyl 8-methylsulfonyl-12-hydroxyheptadecanoate

A solution of diazomethane (approximately 2.5 g., 0.06 mole) in ether (100 ml.) is mixed with a solution of 8-methylsulfonyl-12-hydroxyheptadecanoic acid (10.8 g., 0.03 mole) in ether (50 ml.). The resulting solution is allowed to stand 4 hours at room temperature. Acetic acid is then added to destroy the excess diazomethane and the solution is washed with dilute sodium bicarbonate solution and water and dried over sodium sulfate. Evaporation of volatile materials at reduced pressure yields methyl 8-methylsulfonyl-12-hydroxyheptadecanoate, a colorless viscous oil.

EXAMPLE 33

8-Methylsufonyl-12-acetoxyheptadecanoic acid

A mixture of 8-methylsulfonyl-12-hydroxyheptadecanoic acid (9.1 g., 0.025 mole) and acetic anhydride (0.1 g., 0.06 mole) is heated at 60° C. for 18 hours. The mixture is then cooled and dissolved in 80 ml. ethyl ether. The solution is extracted with an ice-cold solution of 8 g. sodium hydroxide in 150 ml. water. The basic solution is separated and acidified with concentrated hydrochloric acid. The oily acid which separates is taken up in ether, washed with water and dried over sodium sulfate. The ether is evaporated to leave 9.0 g. of the oily crude product.

The product is purified by chromatography on a column containing 150 g. of silica gel and with 1% methanol in chloroform as the eluting solvent. There is obtained 8-methylsulfonyl-12-acetoxyheptadecanoic acid as a colorless viscous oil.

By substituting the acetic anhydride used in Example 32 with an equivalent amount of propionic anhydride, butyric anhydride, isobutyric anhydride, valeric anhydride, or pivalic anhydride and conducting the reaction as described in Example 32, there is obtained 8-methylsulfonyl-12-propionyloxyheptadecanoic acid, 8-methylsulfonyl-12-butyryloxyheptadecanoic acid, 8-methylsulfonyl-12-isobutyryloxyheptadecanoic acid, 8-methylsulfonyl-12-valeryloxyheptadecanoic acid, and 8-methylsulfonyl-12-pivaloyloxyheptadecanoic acid, respectively.

EXAMPLE 34

Preparation of N-(2-dimethylaminoethyl)-8-methylsulfonyl-12-hydroxyheptadecanamide A solution of 8-methylsulfonyl-12-hydroxyheptadecanoic acid (3.6 g., 10 millimole), Example 2, triethylamine (1.74 ml., 12.5 millimole) and distilled water (18 ml., 1.0 mole) in acetonitrile (100 ml.) is treated with N-t-butyl-5-methylisoxazolium perchlorate (3.0 g., 12.5 millimole). The resulting solution is evaporated in vacuo (water aspirator) at 20°-23° C. for 4 hours providing a tacky residue which is triturated with water (150 ml.) at 0°-5° C. for 15 minutes. After decanting the aqueous phase, the oily residue is dissolved in benzene-ether [(1:1), 200 ml.] The organic extract is dried over sodium sulfate, filtered and evaporated in vacuo at 35°-40° C. providing the desired ' active ester ', N-t-butyl-3-(8-methylsulfonyl-12-hydroxyheptadecanoyloxy)crotonamide, as a pale yellow oil.

A solution of 2-dimethylaminoethylamine (0.88 g., 10 millimole) in acetonitrile (25 ml.) is added to a solution of the ' active ester ' in acetonitrile (25 ml.) providing a clear solution which is stirred at 25° C. for 17 hours. The solvent is removed in vacuo at 40°-50° C. leaving a residual oil which is partitioned between ether (200 ml.) and water (2 × 100 ml.). The organic extract is washed with saturated brine (2 × 100 ml.), dried over sodium sulfate, filtered and evaporated in vacuo at 40°-50° C. providing a tan, crude oil.

The oil is partitioned between 5% hydrochloric acid (100 ml.) and ether (2 × 100 ml.). The aqueous acid phase is slowly basified with sodium bicarbonate (16.8 g., 0.2 mole), then with 40% aqueous sodium hydroxide (10 ml.) providing a heterogeneous mixture which is extracted with ether (100 ml.). The ether extract is washed with water and brine and dried over sodium sulfate. The ether is then evaporated in vacuo to leave the title compound as a pale yellow viscous oil.

| CAPSULE FORMULATION | |
|---|---|
| 8-methylsulfonyl-12-hydroxy-heptadecanoic acid | 50 gm. |
| Stearic acid (U.S.P. triple pressure) | 125 gm. |
| Pluronic F-68 | 7.5 gm. |
| Corn starch | 125 gm. |

The stearic acid and pluronic are united in a vessel and melted using a water bath at 60°-65° C. The heating is discontinued and the 8-methylsulfonyl-12-hydroxyheptadecanoic acid is dispersed into the mixture and the corn starch is added with stirring which is continued until the mixture cools to ambient temperature. The mixture is reduced to granules by screening and placed in a number 0 hard gelatin containing 307.5 mg. of total solids and 50 mg. of 8-methylsulfonyl-12-hydroxyheptadecanoic acid per capsule.

EXAMPLE 36

| PARENTERAL FORMULATION OF A MULTIDOSE SOLUTION FOR INTRAMUSCULAR AND INTRAVENOUS USE | |
|---|---|
| 8-methylsulfonyl-12-hydroxy-heptadecanoic acid | 1 gm. |
| Tris(hydroxymethyl)aminomethane (Reagent Grade Tham) | q.s. to adjust solution to pH 7.4 |
| Sodium chloride (U.S.P.) | q.s. to yield isotonic solution |
| Methylparaben | 10 mg. |
| Propylparaben | 1 mg. |
| Distilled water (pyrogen-free) | q.s. to 10 ml. |

The 8-methylsulfonyl-12-hydroxyheptadecanoic acid suspended in about 6 ml. of the water is treated with tris(hydroxymethyl)aminomethane with stirring until the pH reaches 7.4. The methylparaben and propylparaben are added with stirring and sufficient sodium chloride added to produce an isotonic solution. After water is added to bring the final volume to 10 ml., the solution is sterilized by membrane filtration and placed in a vial by an aseptic technique. The solution contains the Tham salt of 8-methylsulfonyl-12-hydroxyheptadecanoic acid equivalent to 100 mg./ml. of the free acid.

EXAMPLE 37

| PREPARATION OF SUPPOSITORIES | |
|---|---|
| 8-methylsulfonyl-12-hydroxy-heptadecanoic acid | 200 gm. |
| Butylated hydroxyanisole | 82 mg. |
| Butylated hydroxytoluene | 82 mg. |
| Ethylenediamine tetraacetic acid | 163 mg. |
| Glycerine, U.S.P. | 128 gm. |
| Sodium chloride, microfine | 52.5 gm. |
| Polyethylene glycol 6000 | 128 gm. |
| Polyethylene glycol 4000 | 1269 gm. |

The polyethylene glycol 4000 and polyethylene glycol 6000 were placed in a vessel surrounded by a water bath at such a temperature required to maintain the melted contents at 60°-65° C. To the melt is added the butylated hydroxyanisole and butylated hydroxytoluene with stirring. Then the ethylenediamine tetraacetic acid and microfine sodium chloride are added to and dispersed in the mixture. The 8-methylsulfonyl-12-hydroxyheptadecanoic acid is then added an dispersed into the mixture. Finally, the temperature is lowered to 55°-60° C. and the glycerine added and dispersed.

While maintaining the temperature of 55°-60° C. and continuous mixing, the melt is dispersed into plastic suppository cavities of a conventional suppository cold-molding device. The suppositories thus prepared contain a total of 1.7778 gm. of contents of which 200 mg. are 8-methylsulfonyl-12-hydroxyheptadecanoic acid.

What is claimed is:

1. The compound of the formula

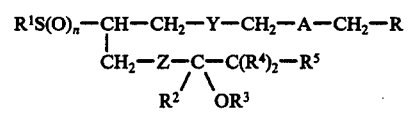

wherein
R is carboxy, a carboxy salt, or a carboxy ester;
A is methylene;
Y is selected from the group consisting of ethylene, vinylene, and ethynylene;
$R^1$ is selected from the group consisting of methyl, ethyl, 2-hydroxyethyl, 2-(loweralkoxy)ethyl, and vinyl;
$n$ is 0, 1, or 2;
Z is selected from the group consisting of ethylene, vinylene, and ethynylene;
$R^2$ is hydrogen or methyl;
$R^3$ is hydrogen;
$R^4$ is hydrogen or methyl;
$R^5$, taken together as a single substituent with $R^2$ and the carbon chain joining $R^2$ and $R^5$, is a carbocyclic ring with from 5-9 members.

2. The compound of claim 1 wherein R is carboxy or a carboxy salt having the formula $-COO^-Me^+$ wherein Me is a pharmaceutically acceptable cation derived from a metal or an amine.

3. The compound of claim 2 wherein
$n$ is 0, and $R^1$ is methyl or hydroxyethyl.

4. The compound of claim 3 wherein
Y is ethylene,
A is methylene,
Z is ethylene,
$R^2$, $R^3$ and $R^4$ are hydrogen, and
R is carboxy.

5. The compound of claim 2 wherein $n$ is 1.

6. The compound of claim 2 wherein $n$ is 2.

7. The compound of claim 6 wherein
Y is ethylene,
A is methylene,
R is carboxy, and
$R^1$ is methyl.

8. The compound of claim 7 wherein Z is ethynylene.

9. The compound of claim 8 wherein
$R^2$, $R^3$, and $R^4$ are each hydrogen, and
$R^5$ is 4-carbon straight chain alkyl joined through the terminal carbon with abstraction of hydrogen to the carbon bearing the $R^2$ and $OR^3$ substituents,
which is 8-methylsulfonyl-11-(1-hydroxycyclohexyl)-10-undecynoic acid.

10. The compound of claim 6 wherein
Y is ethylene,
A is methylene,
Z is ethylene,
R is carboxy,
$R^1$ is methyl, and
$R^3$ and $R^4$ are hydrogen.

11. The compound of claim 10 wherein $R^2$ and $R^5$ taken together form a tetramethylene radical, which is 8-methylsulfonyl-11-(1-hydroxycyclohexyl)undecanoic acid.

* * * * *